United States Patent
Ni et al.

(10) Patent No.: US 12,157,014 B2
(45) Date of Patent: Dec. 3, 2024

(54) RADIATION THERAPY SYSTEM AND METHOD

(71) Applicant: SHANGHAI UNITED IMAGING HEALTHCARE CO., LTD., Shanghai (CN)

(72) Inventors: Cheng Ni, Shanghai (CN); Peng Cheng, Shanghai (CN); Shoubo He, Shanghai (CN); Gang Pan, Shanghai (CN); Peng Wang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 445 days.

(21) Appl. No.: 17/445,951

(22) Filed: Aug. 25, 2021

(65) Prior Publication Data

US 2021/0393983 A1 Dec. 23, 2021

Related U.S. Application Data

(63) Continuation of application No. PCT/CN2020/096467, filed on Jun. 17, 2020.

(51) Int. Cl.
*A61N 5/10* (2006.01)
*A61N 5/00* (2006.01)

(52) U.S. Cl.
CPC ...... *A61N 5/1039* (2013.01); *A61N 2005/005* (2013.01); *A61N 2005/1089* (2013.01); *A61N 2005/1094* (2013.01)

(58) Field of Classification Search
CPC ............ A61N 5/1039; A61N 2005/005; A61N 2005/1089; A61N 2005/1094;
(Continued)

(56) References Cited

U.S. PATENT DOCUMENTS

| 3,867,635 A | 2/1975 | Brown et al. |
| 6,366,798 B2 | 4/2002 | Green |

(Continued)

FOREIGN PATENT DOCUMENTS

| CN | 103140013 A | 6/2013 |
| CN | 105233425 A | 1/2016 |

(Continued)

OTHER PUBLICATIONS

First Office Action in Chinese Application No. 202080018003.1 mailed on Jun. 6, 2022, 16 pages.
(Continued)

*Primary Examiner* — David P Porta
*Assistant Examiner* — Mamadou Faye
(74) *Attorney, Agent, or Firm* — METIS IP LLC

(57) ABSTRACT

The present disclosure is directed to a radiation therapy system. The radiation therapy system may comprise a magnetic resonance imaging (MRI) apparatus. The MRI apparatus may include a plurality of shielding magnetic coils, the plurality of shielding magnetic coils being arranged around an axis. The radiation therapy system may also comprise a radiation therapy apparatus, which includes a linear accelerator configured to accelerate electrons to produce a radiation beam, the linear accelerator being located between two neighboring shielding coils of the plurality of shielding coils, and a length direction of the linear accelerator being parallel with the axis. The radiation therapy apparatus may also include a deflection magnet configured to deflect the electrons emitted from the linear accelerator by a deflection angle in a first portion of a moving trajectory, the first portion of the moving trajectory being on a plane intersecting with a radial plane of the MRI apparatus.

19 Claims, 12 Drawing Sheets

(58) Field of Classification Search
CPC .............. A61N 5/1067; A61N 5/1049; A61N 2005/1055; A61N 5/10; A61B 5/055; G01R 33/44
See application file for complete search history.

(56) References Cited

U.S. PATENT DOCUMENTS

| | | |
|---|---|---|
| 6,977,987 B2 | 12/2005 | Yamashita et al. |
| 7,394,254 B2 | 7/2008 | Rieke et al. |
| 8,958,864 B2 | 2/2015 | Amies et al. |
| 2005/0197564 A1 | 9/2005 | Dempsey |
| 2006/0273795 A1 | 12/2006 | Rieke et al. |
| 2008/0208036 A1 | 8/2008 | Amies et al. |
| 2011/0213239 A1* | 9/2011 | Amies ............... A61N 5/1049 600/411 |
| 2012/0165652 A1* | 6/2012 | Dempsey ............ A61N 5/1067 600/410 |
| 2014/0128719 A1 | 5/2014 | Longfield |
| 2014/0135615 A1* | 5/2014 | Kruip ................. A61N 5/1081 600/411 |
| 2014/0159719 A1 | 6/2014 | Chon |
| 2014/0257099 A1* | 9/2014 | Balakin ................ H05H 7/08 600/436 |
| 2014/0378826 A1 | 12/2014 | Edelman |
| 2017/0176560 A1 | 6/2017 | Zho et al. |
| 2018/0099160 A1 | 4/2018 | Forton |
| 2019/0060670 A1 | 2/2019 | Ni et al. |
| 2020/0230439 A1* | 7/2020 | Liu ..................... A61N 5/1037 |
| 2021/0031055 A1* | 2/2021 | Jiang .................... A61B 5/055 |

FOREIGN PATENT DOCUMENTS

| | | |
|---|---|---|
| CN | 105636331 A | 6/2016 |
| CN | 105939566 A | 9/2016 |
| CN | 107789749 A | 3/2018 |
| GB | 2427478 A | 12/2006 |
| JP | S63315072 A | 12/1988 |
| JP | 2004065808 A | 3/2004 |
| WO | 2012049466 A1 | 4/2012 |
| WO | 2020097821 A1 | 5/2020 |

OTHER PUBLICATIONS

International Search Report in PCT/CN2020/096467 mailed on Mar. 15, 2021, 4 pages.
Written Opinion in PCT/CN2020/096467 mailed on Mar. 15, 2021, 5 pages.
The Extended European Search Report in European Application No. 20940755.0 mailed on May 22, 2023, 7 pages.

* cited by examiner

RADIATION THERAPY SYSTEM AND METHOD

CROSS-REFERENCE TO RELATED APPLICATIONS

This application is a continuation of International Patent Application No. PCT/CN2020/096467, filed on Jun. 17, 2020, the contents of which are hereby incorporated by reference.

TECHNICAL FIELD

The present disclosure generally relates to a radiation therapy system, and more particularly, relates to an image-guided radiation therapy system that combines radiation therapy and magnetic resonance imaging techniques.

BACKGROUND

Radiation therapy on a subject (e.g., a tumor) is currently affected by difficulties to track the variation (e.g., motion) of the subject in different treatment sessions. Nowadays, various imaging techniques may be applied to provide real-time images of the subject before or within each treatment session. For example, a magnetic resonance imaging (MRI) apparatus may be used in combination with a radiation therapy apparatus to provide MR images of the subject. The combination of the MRI apparatus and the radiation therapy apparatus, which forms an MRI image-guided therapeutic apparatus, may encounter difficulties in arranging components of the MRI apparatus (e.g., a plurality of main magnetic coils, a plurality of shielding magnetic coils, one or more gradient coils, etc.) and components of the radiation therapy apparatus (e.g., a linear accelerator) in a relatively compact space without causing interferences. Therefore, it may be desirable to provide a therapeutic apparatus that provides high therapeutic quality and also has a compact structure as well.

SUMMARY

According to an aspect of the present disclosure, a radiation therapy system is provided. The radiation therapy system may comprise a magnetic resonance imaging (MRI) apparatus configured to acquire MRI data with respect to a region of interest (ROI) of a subject. The MRI apparatus may include a plurality of shielding magnetic coils, the plurality of shielding magnetic coils being arranged around an axis. The radiation therapy system may also comprise a radiation therapy apparatus configured to apply therapeutic radiation to at least one portion of the ROI. The radiation therapy apparatus may include a linear accelerator configured to accelerate electrons to produce a radiation beam, the linear accelerator being located between two neighboring shielding coils of the plurality of shielding coils, and a length direction of the linear accelerator being parallel with the axis; and a deflection magnet configured to deflect the electrons emitted from the linear accelerator by a deflection angle in a first portion of a moving trajectory, the first portion of the moving trajectory being on a plane intersecting with a radial plane of the MRI apparatus.

In some embodiments, the deflection magnet includes at least one electromagnet, the at least one electromagnet being configured to correct dispersion of the electrons.

In some embodiments, the deflection magnet includes at least one arc-shaped deflection channel on the plane, an inlet of a forefront arc-shaped deflection channel of the at least one deflection channel being aligned with an outlet of the linear accelerator, and the electrons being deflected by the deflection angle in the at least one arc-shaped deflection channel.

In some embodiments, the electrons emitted from a rearmost arc-shaped deflection channel of the at least one arc-shaped deflection channel are deflected to a target in a second portion of the moving trajectory, the second portion of the moving trajectory being within a main magnetic field generated by a plurality of main magnetic coils, the direction of the main magnetic field being parallel with the axis.

In some embodiments, the radiation therapy apparatus further includes one or more correction coils along at least one of the first portion or the second portion of the moving trajectory, the one or more correction coils being configured to correct the moving trajectory so that the electrons collide onto the target substantially vertically.

In some embodiments, the deflection angle is 270 degrees.

In some embodiments, a center line of an accelerating tube of the linear accelerator is spaced apart from a line that is along a radial direction of the MRI apparatus, the line passing through the target.

In some embodiments, an accelerating tube of the linear accelerator and the target correspond to different circumferential positions of the MRI apparatus.

In some embodiments, the MRI apparatus further includes an annular cryostat in which a plurality of main magnetic coils and the plurality of shielding coils are located, the plurality of main magnetic coils, the plurality of shielding coils, and the annular cryostat being coaxially arranged.

In some embodiments, the annular cryostat includes an outer wall, an inner wall, and a recess between the outer wall and the inner wall, the recess having an opening formed at the outer wall, the linear accelerator being at least partially located within the annular recess.

In some embodiments, the recess is a through hole along a radial direction of the MRI apparatus.

In some embodiments, the MRI apparatus further includes one or more gradient coils arranged in a bore formed by the annular cryostat, the one or more gradient coils being around the axis.

In some embodiments, the one or more gradient coils are split gradient coils.

In some embodiments, the plane where the first portion of the moving trajectory is located is substantially perpendicular to a radial plane of the MRI apparatus.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections or assembly of different levels in ascending order. However, the terms may be displaced by another expression if they achieve the same purpose.

Figure 3:
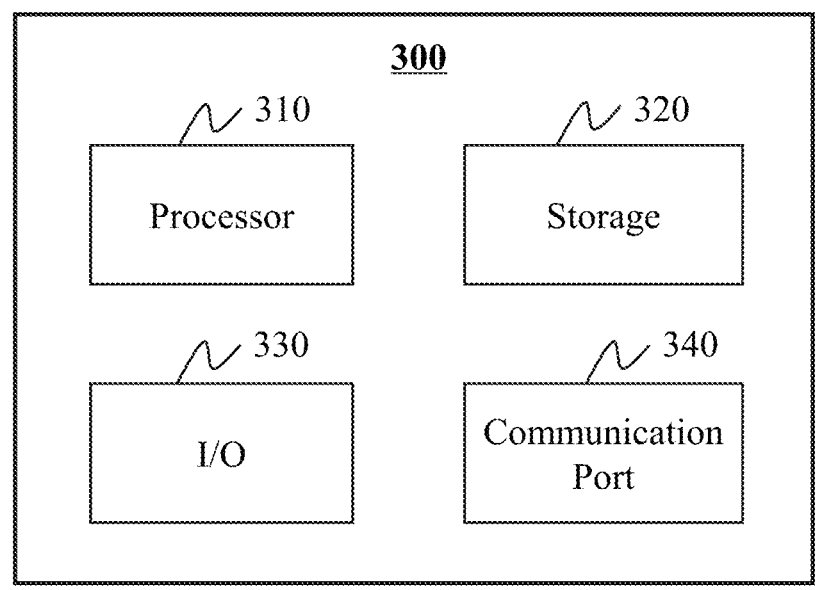
FIG. 3 is a schematic diagram illustrating exemplary hardware and/or software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 310 as illustrated in FIG. 3) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

It will be understood that, although the terms "first," "second," "third," etc., may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are apparatus for medical application, such as for disease treatment and/or diagnostic purposes. While the apparatus disclosed in the present disclosure are described primarily regarding a magnetic resonance imaging-radiotherapy (MRI-RT) system. It should be understood that this is only for illustration purposes. In some embodiments, the imaging system may include a positron emission tomograhy-radiotherapy (PET-RT) system, an emission computed tomography-radiothreraphy (ECT-RT) system, a computed tomography-radiotheraphy (CT-RT) system, etc.

An aspect of the present disclosure relates to a radiation therapy system. The radiation therapy system may include an MRI apparatus and a radiation therapy apparatus. The MRI apparatus may include a plurality of main magnetic coils and a plurality of shielding coils. The plurality of main magnetic coils may be arranged around an axis. The plurality of shielding magnetic coils may be arranged coaxially with the plurality of main magnetic coils, with a larger radius from the axis than the plurality of main magnetic coils. The radiation therapy apparatus may include a linear accelerator and a deflection device. The linear accelerator may be located between two neighboring shielding coils of the plurality of shielding coils. In this case, a source-to-axis distance (SAD) from a radiation source of the radiation therapy apparatus to a rotation axis of the gantry may be smaller than that of conventional MRI-RT systems. And a length direction of the linear accelerator may be parallel with the axis. The length direction of the linear accelerator may be parallel with the direction of magnetic field generated by the plurality of main magnetic coils and the plurality of shielding coils. Thus, the effect of the magnetic field on the acceleration of electrons in the linear accelerator may be removed or reduced, and magnetic shielding for the linear accelerator may be omitted.

The deflection magnet may be configured to deflect the electrons emitted from the linear accelerator by a deflection angle in a first portion of a moving path, and the first portion of the moving path being on a plane intersecting with (e.g., substantially perpendicular to) a radial plane of the MRI apparatus. In this way, an area (e.g., a recess on a magnetic body of the MRI apparatus) for placing at least in part of one or more components of the radiation therapy apparatus (e.g., the linear accelerator and/or the deflection magnet) between the two neighboring shielding coils of the plurality of shielding coils may be minimized, such that the homogeneity of the magnetic field generated by the plurality of main magnetic coils and the plurality of shielding coils may be improved, and the effect of the area on the imaging of the subject using the MRI apparatus may be removed or reduced.

Figure 1:
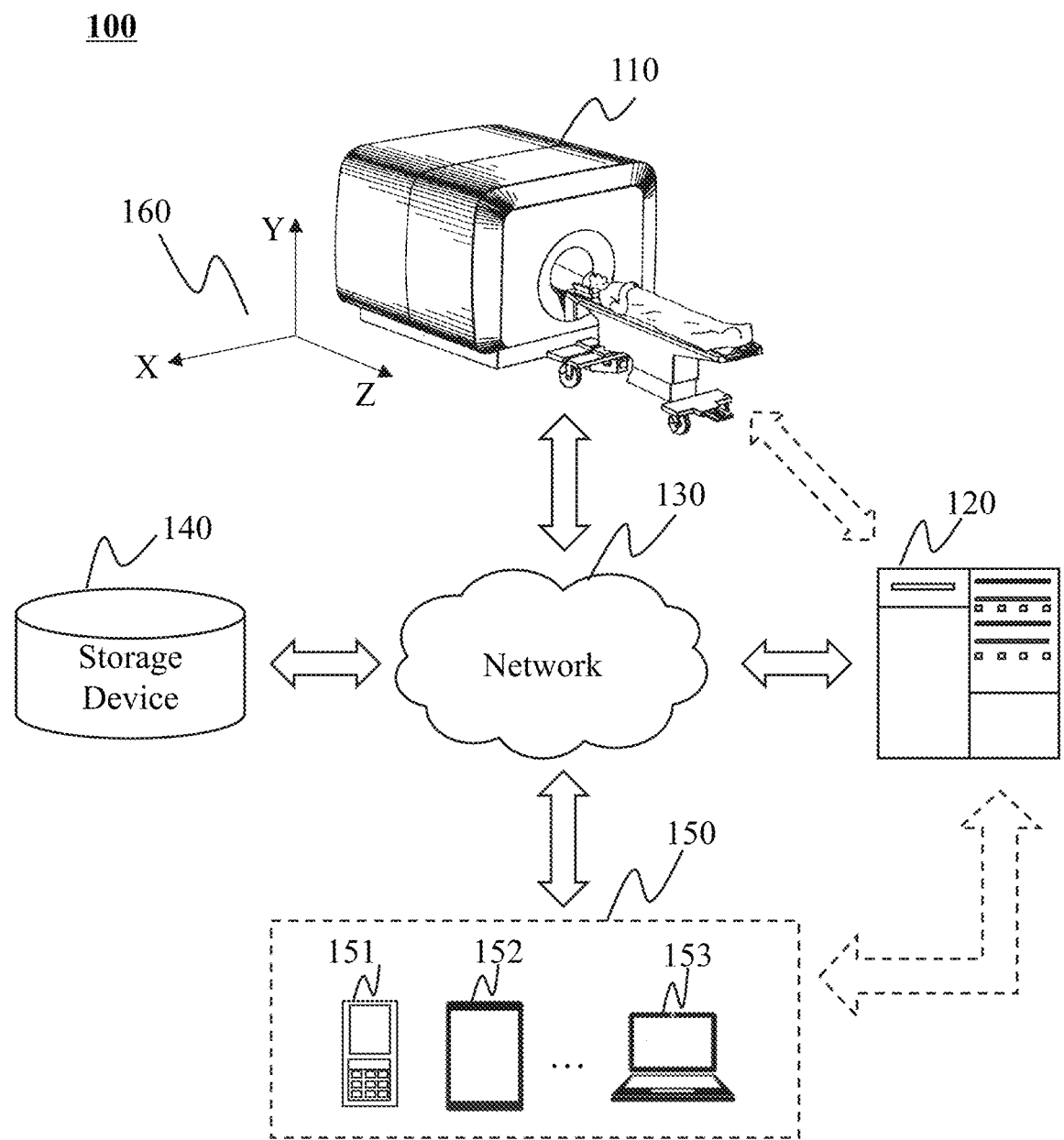
FIG. 1 is a block diagram illustrating an exemplary radiation therapy system according to some embodiments of the present disclosure.

FIG. 1 is a block diagram illustrating an exemplary radiation therapy system 100 according to some embodiments of the present disclosure. In some embodiments, the radiation therapy system 100 may be a multi-modality imaging system including, for example, a magnetic resonance imaging-radiotherapy (MRI-RT) system, a positron emission tomograhy-radiotherapy (PET-RT) system, etc. For better understanding the present disclosure, an MRI-RT system may be described as an example of the radiation therapy system 100, and not intended to limit the scope of the present disclosure.

As shown in FIG. 1, the radiation therapy system 100 may include a therapeutic apparatus 110, one or more processing devices 120, a network 130, a storage device 140, and one or more terminal devices 150. In some embodiments, the therapeutic apparatus 110, the one or more processing devices 120, the storage device 140, and/or the terminal device 150 may be connected to and/or communicate with each other via a wireless connection (e.g., the wireless connection provided by the network 130), a wired connection (e.g., the wired connection provided by the network 130), or any combination thereof.

The therapeutic apparatus 110 may include an MRI apparatus. The MRI apparatus may generate image data associated with MR signals generated by scanning a subject or a portion thereof. In some embodiments, the subject may include a body, a substance, an object, or the like, or any combination thereof. In some embodiments, the subject may include a specific portion of a body, a specific organ, or specific tissue, etc. For example, the subject may include the head, the brain, the neck, the body, shoulders, arms, the thorax, the cardiac, the stomach, blood vessels, soft tissue, knees, feet, etc., of a patient. The MRI apparatus may include a permanent magnet MRI scanner, a superconducting electromagnet MRI scanner, or a resistive electromagnet MRI scanner, etc., according to a type of a magnetic body of the MRI apparatus. In some embodiments, the MRI apparatus may include a high-field MRI scanner, a mid-field MRI scanner, and a low-field MRI scanner, etc., according to an intensity of the magnetic field generated by the MRI apparatus. In some embodiments, the MRI apparatus may be of a closed-bore (cylindrical) type, an open-bore type, or the like. In some embodiments, the therapeutic apparatus 110 may transmit, via the network 130, the image data to the one or more processing devices 120, the storage device 140, and/or the terminal device 150 for further processing. For example, the image data may be sent to the one or more processing devices 120 for generating an MR image, or may be stored in the storage device 140.

For illustration purposes, a coordinate system 160 including an X axis, a Y axis, and a Z axis (also referred to as X direction, Y direction, and Z direction, respectively) is provided in FIG. 1. The X axis and the Z axis shown in FIG. 1 may be horizontal, and the Y axis may be vertical. As illustrated, the positive X direction along the X axis may be from the right side to the left side of the therapeutic apparatus 110 seen from the direction facing the front side of the therapeutic apparatus 110; the positive Y direction along the Y axis shown in FIG. 1 may be from the lower part to the upper part of the therapeutic apparatus 110; the positive Z direction along the Z axis shown in FIG. 1 may refer to a direction from the back side to the front side of the therapeutic apparatus 110, in which the subject is moved out of an imaging or treatment channel (or referred to as an imaging or treatment bore) of the therapeutic apparatus 110.

In some embodiments, the MRI apparatus of the therapeutic apparatus 110 may be directed to select an anatomical slice of the subject along a slice selection direction and scan the anatomical slice to acquire a plurality of echo signals from the slice. During the scan, spatial encoding within the slice may be implemented by spatial encoding coils (e.g., an X coil and a Y coil) along a phase encoding direction and a frequency encoding direction. The echo signals may be sampled and the corresponding sampled data may be stored into a K-space matrix for generating image data of the subject or a portion thereof. For illustration purposes, the slice-selection direction herein may correspond to the Z direction defined by the coordinate system 160 and a Kz direction in K-space; the phase-encoding direction may correspond to the Y direction defined by the coordinate system 160 and a Ky direction in K-space; and the frequency-encoding direction may correspond to the X direction defined by the coordinate system 160 and a Kx direction in K-space. It should be noted that the slice-selection direction, the phase-encoding direction, and the frequency-encoding direction may be modified according to actual needs, and the modification may do not depart the scope of the present disclosure. More description of the MRI apparatus may be found elsewhere in the present disclosure. See, e.g., FIG. 2A and the description thereof.

The therapeutic apparatus 110 may also include a radiation therapy apparatus. The radiation therapy apparatus may apply a therapeutic radiation beam to a target region of the subject. The therapeutic radiation beam may include a particle ray beam, a photon ray beam, etc. Exemplary particle rays may include neutron, proton, electron, μ-meson, heavy ion, α-ray, or the like, or any combination thereof. Exemplary photon rays may include X-ray, γ-ray, ultraviolet, laser, or the like, or any combination thereof. For illustration purposes, a radiation therapy apparatus providing an X-ray beam may be described as an example.

In some embodiments, the radiation therapy apparatus may be operably coupled to the MRI apparatus. In some embodiments, one or more components of the radiation therapy apparatus may be arranged at least in part in the MRI apparatus. For example, a linear accelerator of the radiation therapy apparatus may be between two neighboring shielding coils of a plurality of shielding coils of the MRI apparatus. As another example, one or more components of the radiation therapy apparatus may be arranged at least in part in an area (e.g., a recess on a magnetic body of the MRI apparatus) between of the two neighboring shielding coils.

In some embodiments, the MRI apparatus may acquire image data of the subject before, during, and/or after at least a portion of a radiation therapy is performed on the subject. The radiation therapy apparatus may apply the therapeutic radiation beam to the target region of the subject based at least in part on the image data provided by the MRI apparatus. Since radiation therapy on target region may be affected by difficulties to track the variation (e.g., motion) of the target region in different treatment sessions. The image data provided by the MRI apparatus may be applied to provide substantially real-time images of the target region before or within the treatment sessions. For example, the image data may be reconstructed to generate an image of the subject so as to locate the target region of the subject and/or determine the dose of the X-ray beam. As another example, the MRI image data, without being reconstructed to an MRI image, may be used to identify a motion of the subject, which may be used to guide the delivery of the therapeutic radiation beam to the target region of the subject.

The subject may be placed on a treatment table. The treatment table may support the subject for imaging using the MRI apparatus and/or radiation treatment using the radiation therapy apparatus. The treatment table may be moveable back and forth along a longitudinal direction (i.e., the Z direction in FIG. 1) of the treatment table. The longitudinal direction of the treatment table may be parallel to an axial direction of the bore of the MRI apparatus. If the subject needs to be treated, the treatment table carrying the subject may be moved to a treatment position. If the subject needs to be imaged, the treatment table carrying the subject may be moved to an imaging position.

The one or more processing devices 120 may process data and/or information obtained from the therapeutic apparatus 110, the storage device 140, and/or the terminal device 150. For example, the one or more processing devices 120 may process image data, and reconstruct at least one MR image based on the image data. As another example, the one or more processing devices 120 may determine a position of a treatment region and a dose of radiation to be delivered to the treatment region based on the at least one MR image. The MR image may have advantages such as a superior soft-tissue contrast, a high resolution, and geometric accuracy, which may allow accurate positioning of the treatment region. The MR image may be used to detect a variance of the treatment region (e.g., a variance of the thorax due to the breath of the subject) during the radiation therapy, such that a treatment plan of the radiation therapy may be adjusted accordingly.

In the treatment plan, the dose of radiation may be determined according to, for example, synthetic electron density information. In some embodiments, the synthetic electron density information may be generated based on the MR image.

In some embodiments, the one or more processing devices 120 may be a single processing device that communicates with and process data from the MRI apparatus and the radiation therapy apparatus of the therapeutic apparatus 110. In some embodiments, the one or more processing devices 120 may include at least two processing devices. One of the at least two processing devices may communicate with and process data from the MRI apparatus of the therapeutic apparatus 110, and another one of the at least two processing devices may communicate with and process data from the radiation therapy apparatus of the therapeutic apparatus 110. The at least two processing devices may communicate with each other.

In some embodiments, the one or more processing devices 120 may be a single server or a server group. The server group may be centralized or distributed. In some embodiments, the one or more processing devices 120 may be local to or remote from the therapeutic apparatus 110. For example, the one or more processing devices 120 may access information and/or data from the therapeutic apparatus 110, the storage device 140, and/or the terminal device 150 via the network 130. As another example, the one or more processing devices 120 may be directly connected to the therapeutic apparatus 110, the terminal device 150, and/or the storage device 140 to access information and/or data. In some embodiments, the one or more processing devices 120 may be implemented on a cloud platform. The cloud platform may include a private cloud, a public cloud, a hybrid cloud, a community cloud, a distributed cloud, an inter-cloud, a multi-cloud, or the like, or any combination thereof.

The network 130 may include any suitable network that can facilitate the exchange of information and/or data for the radiation therapy system 100. In some embodiments, one or more components of the radiation therapy system 100 (e.g., the therapeutic apparatus 110, the one or more processing devices 120, the storage device 140, or the terminal device 150) may communicate information and/or data with one or more other components of the radiation therapy system 100 via the network 130. For example, the one or more processing devices 120 may obtain image data from the therapeutic apparatus 110 via the network 130. As another example, the one or more processing devices 120 may obtain user instructions from the terminal device 150 via the network 130. The network 130 may include a public network (e.g., the Internet), a private network (e.g., a local area network (LAN), a wide area network (WAN)), a wired network (e.g., an Ethernet network), a wireless network (e.g., an 802.11 network, a Wi-Fi network), a cellular network (e.g., a Long Term Evolution (LTE) network), a frame relay network, a virtual private network ("VPN"), a satellite network, a telephone network, routers, hubs, switches, server computers, or the like, or any combination thereof. In some embodiments, the network 130 may include one or more network access points. For example, the network 130 may include wired and/or wireless network access points such as base stations and/or internet exchange points through which one or more components of the radiation therapy system 100 may be connected to the network 130 to exchange data and/or information.

The storage device 140 may store data, instructions, and/or any other information. In some embodiments, the storage device 140 may store data obtained from the one or more processing devices 120 and/or the terminal device 150. In some embodiments, the storage device 140 may store data and/or instructions that the one or more processing devices 120 may execute or use to perform exemplary methods described in the present disclosure. In some embodiments, the storage device 140 may include a mass storage device, a removable storage device, a cloud based storage device, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), a digital versatile disk ROM, etc. In some embodiments, the storage device 140 may be implemented on a cloud platform as described elsewhere in the present disclosure.

In some embodiments, the storage device 140 may be connected to the network 130 to communicate with one or more other components of the radiation therapy system 100 (e.g., the one or more processing devices 120 or the terminal device 150). One or more components of the radiation therapy system 100 may access the data or instructions stored in the storage device 140 via the network 130. In some embodiments, the storage device 140 may be part of the one or more processing devices 120.

The terminal device 150 may be connected to and/or communicate with the therapeutic apparatus 110, the one or more processing devices 120, and/or the storage device 140. For example, the one or more processing devices 120 may acquire a treatment plan from the terminal device 150. As another example, the terminal device 150 may obtain image data from the therapeutic apparatus 110 and/or the storage device 140. In some embodiments, the terminal device 150 may include a mobile device 151, a tablet computer 152, a laptop computer 153, or the like, or any combination thereof. For example, the mobile device 151 may include a mobile phone, a personal digital assistance (PDA), a laptop, a tablet computer, a desktop, or the like, or any combination thereof. In some embodiments, the terminal device 150 may include an input device, an output device, etc. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to the one or more processing devices 120 via, for example, a bus, for further processing. Other types of the input device may include a cursor control device, such as a mouse, a trackball, or cursor direction keys, etc. The output device may include a display, a speaker, a printer, or the like, or any combination thereof. In some embodiments, the terminal device 150 may be part of the one or more processing devices 120.

This description is intended to be illustrative, and not to limit the scope of the present disclosure. Many alternatives, modifications, and variations will be apparent to those skilled in the art. The features, structures, methods, and characteristics of the exemplary embodiments described herein may be combined in various ways to obtain additional and/or alternative exemplary embodiments. For example, the storage device 140 may be a data storage including cloud computing platforms, such as public cloud, private cloud, community, hybrid clouds, etc. In some embodiments, the one or more processing devices 120 may be integrated into the therapeutic apparatus 110. As another example, the radiation therapy system 100 may further include a control device configured to determine one or more parameters of the therapeutic apparatus 110 so as to optimize the imaging and/or radiation treatment of the subject. In some embodiments, the control device may be part of the processing device 120 and/or the terminal 150. However, those variations and modifications do not depart the scope of the present disclosure.

Figure 2A:
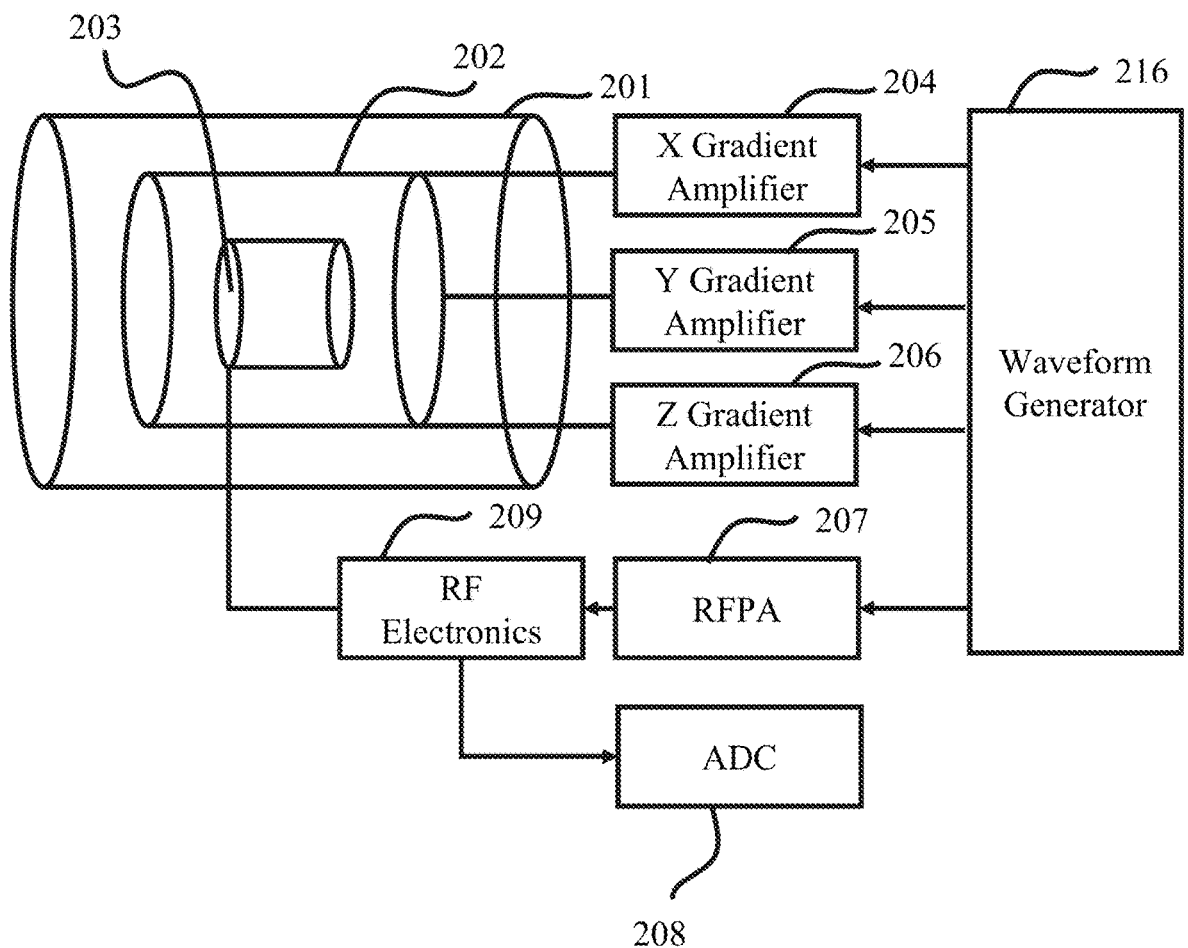
FIG. 2A is a schematic diagram illustrating exemplary components of an MRI apparatus according to some embodiments of the present disclosure.

FIG. 2A is a schematic diagram illustrating exemplary components of an MRI apparatus according to some embodiments of the present disclosure. One or more components of the MRI apparatus 200 are illustrated in FIG. 2A. As illustrated, a main magnet 201 may generate a first magnetic field (or referred to as a main magnetic field) that may be applied to a subject (also referred to as an object) exposed inside the field. The main magnet 201 may include a resistive magnet or a superconductive magnet that both need a power supply (not shown) for operation. Alternatively, the main magnet 201 may include a permanent magnet. The main magnet 201 may include a bore within which the subject is placed. The main magnet 201 may also control the homogeneity of the generated main magnetic field. One or more shim coils may be in the main magnet 201. The shim coils placed in the gap of the main magnet 201 may compensate for the inhomogeneity of the magnetic field of the main magnet 201. The shim coils may be energized by a shim power supply.

Gradient coils 202 may be located inside the main magnet 201. The gradient coils 202 may generate a second magnetic field (or referred to as a gradient field, including gradient fields Gx, Gy, and Gz). The second magnetic field may be superimposed on the main field generated by the main magnet 201 and distort the main field so that the magnetic orientations of the protons of a subject may vary as a function of their positions inside the gradient field, thereby encoding spatial information into echo signals generated by the region of the subject being imaged. The gradient coils 202 may include X coils (e.g., configured to generate the gradient field Gx corresponding to the X direction), Y coils (e.g., configured to generate the gradient field Gy corresponding to the Y direction), and/or Z coils (e.g., configured to generate the gradient field Gz corresponding to the Z direction) (not shown in FIG. 2A). In some embodiments, the Z coils may be designed based on circular (Maxwell)

coils, while the X coils and the Y coils may be designed on the basis of the saddle (Golay) coil configuration. The three sets of coils may generate three different magnetic fields that are used for position encoding. The gradient coils 202 may allow spatial encoding of echo signals for image construction. The gradient coils 202 may be connected with one or more of an X gradient amplifier 204, a Y gradient amplifier 205, or a Z gradient amplifier 206. One or more of the three amplifiers may be connected to a waveform generator 216. The waveform generator 216 may generate gradient waveforms that are applied to the X gradient amplifier 204, the Y gradient amplifier 205, and/or the Z gradient amplifier 206. An amplifier may amplify a waveform. An amplified waveform may be applied to one of the coils in the gradient coils 202 to generate a magnetic field in the X-axis, the Y-axis, or the Z-axis, respectively. The gradient coils 202 may be designed for either a close-bore MR scanner or an open-bore MR scanner. In some instances, all three sets of coils of the gradient coils 202 may be energized and three gradient fields may be generated thereby. In some embodiments of the present disclosure, the X coils and Y coils may be energized to generate the gradient fields in the X direction and the Y direction. As used herein, the X-axis, the Y-axis, the Z-axis, the X direction, the Y direction, and the Z direction in the description of FIG. 2A are the same as or similar to those described in FIG. 1.

In some embodiments, radio frequency (RF) coils 203 may be located inside the main magnet 201 and serve as transmitters, receivers, or both. The RF coils 203 may be in connection with RF electronics 209 that may be configured or used as one or more integrated circuits (ICs) functioning as a waveform transmitter and/or a waveform receiver. The RF electronics 209 may be connected to a radiofrequency power amplifier (RFPA) 207 and an analog-to-digital converter (ADC) 208.

When used as transmitters, the RF coils 203 may generate RF signals that provide a third magnetic field that is utilized to generate echo signals related to the region of the subject being imaged. The third magnetic field may be perpendicular to the main magnetic field. The waveform generator 216 may generate an RF pulse. The RF pulse may be amplified by the RFPA 207, processed by the RF electronics 209, and applied to the RF coils 203 to generate the RF signals in response to a powerful current generated by the RF electronics 209 based on the amplified RF pulse.

When used as receivers, the RF coils may be responsible for detecting echo signals. After excitation, the echo signals generated by the subject may be sensed by the RF coils 203. The receive amplifier then may receive the sensed echo signals from the RF coils 203, amplify the sensed echo signals, and provide the amplified echo signals to the ADC 208. The ADC 208 may transform the echo signals from analog signals to digital signals. The digital echo signals then may be sent to the processing device 120 for sampling.

In some embodiments, the gradient coils 202 and the RF coils 203 may be circumferentially positioned with respect to the subject. It is understood by those skilled in the art that the main magnet 201, the gradient coils 202, and the RF coils 203 may be situated in a variety of configurations around the subject.

In some embodiments, the RFPA 207 may amplify an RF pulse (e.g., the power of the RF pulse, the voltage of the RF pulse) such that an amplified RF pulse is generated to drive the RF coils 203. The RFPA 207 may include a transistor-based RFPA, a vacuum tube-based RFPA, or the like, or any combination thereof. The transistor-based RFPA may include one or more transistors. The vacuum tube-based RFPA may include a triode, a tetrode, a klystron, or the like, or any combination thereof. In some embodiments, the RFPA 207 may include a linear RFPA, or a nonlinear RFPA. In some embodiments, the RFPA 207 may include one or more RFPAs.

In some embodiments, the MRI apparatus 200 may further include a subject positioning system (not shown). The subject positioning system may include a subject cradle and a transport device. The subject may be placed on the subject cradle and be positioned by the transport device within the bore of the main magnet 201.

An MRI apparatus (e.g., the MRI apparatus 200 disclosed in the present disclosure) may be commonly used to obtain an interior image from a patient for a particular region of interest (ROI) that can be used for the purposes of, e.g., diagnosis, treatment, or the like, or a combination thereof. The MRI apparatus may include a main magnet (e.g., the main magnet 201) assembly for providing a strong uniform main magnetic field to align the individual magnetic moments of the H atoms within the patient's body. During this process, the H atoms oscillate around their magnetic poles at their characteristic Larmor frequency. If the tissue is subjected to an additional magnetic field, which is tuned to the Larmor frequency, the H atoms absorb additional energy, which rotates the net aligned moment of the H atoms. The additional magnetic field may be provided by an RF excitation signal (e.g., the RF signal generated by the RF coils 203). When the additional magnetic field is removed, the magnetic moments of the H atoms rotate back into alignment with the main magnetic field thereby emitting an echo signal. The echo signal is received and processed to form an MR image. T1 relaxation may be the process by which the net magnetization grows/returns to its initial maximum value parallel to the main magnetic field. T1 may be the time constant for regrowth of longitudinal magnetization (e.g., along the main magnetic field). T2 relaxation may be the process by which the transverse components of magnetization decay or dephase. T2 may be the time constant for decay/dephasing of transverse magnetization.

If the main magnetic field is uniform across the entire body of the patient, then the RF excitation signal may excite all of the H atoms in the sample non-selectively. Accordingly, in order to image a particular portion of the patient's body, magnetic field gradients Gx, Gy, and Gz (e.g., generated by the gradient coils 202) in the x, y, and z directions, having a particular timing, frequency, and phase, may be superimposed on the uniform magnetic field such that the RF excitation signal excites the H atoms in a desired slice of the patient's body, and unique phase and frequency information is encoded in the echo signal depending on the location of the H atoms in the "image slice".

Typically, portions of the patient's body to be imaged are scanned by a sequence of measurement cycles in which the RF excitation signals and the magnetic field gradients Gx, Gy and Gz vary according to an MRI imaging protocol that is being used. A protocol may be designed for one or more tissues to be imaged, diseases, and/or clinical scenarios. A protocol may include a certain number of pulse sequences oriented in different planes and/or with different parameters. The pulse sequences may include spin echo sequences, gradient echo sequences, diffusion sequences, inversion recovery sequences, or the like, or any combination thereof. For instance, the spin echo sequences may include a fast spin echo (FSE) pulse sequence, a turbo spin echo (TSE) pulse sequence, a rapid acquisition with relaxation enhancement (RARE) pulse sequence, a half-Fourier acquisition single-shot turbo spin-echo (HASTE) pulse sequence, a turbo gradient spin echo (TGSE) pulse sequence, or the like, or any combination thereof. As another example, the gradient echo sequences may include a balanced steady-state free precession (bSSFP) pulse sequence, a spoiled gradient echo (GRE) pulse sequence, and an echo planar imaging (EPI) pulse sequence, a steady state free precession (SSFP), or the like, or any combination thereof. The protocol may also include information regarding image contrast and/or ratio, an ROI, slice thickness, an imaging type (e.g., T1 weighted imaging, T2 weighted imaging, proton density weighted imaging, etc.), T1, T2, an echo type (spin echo, fast spin echo (FSE), fast recovery FSE, single shot FSE, gradient recalled echo, fast imaging with stead-state procession, and so on), a flip angle value, acquisition time (TA), echo time (TE), repetition time (TR), echo train length (ETL), the number of phases, the number of excitations (NEX), inversion time, bandwidth (e.g., RF receiver bandwidth, RF transmitter bandwidth, etc.), or the like, or any combination thereof. For each MRI scan, the resulting echo signals may be digitized and processed to reconstruct an image in accordance with the MRI imaging protocol that is used.

Figure 2B:
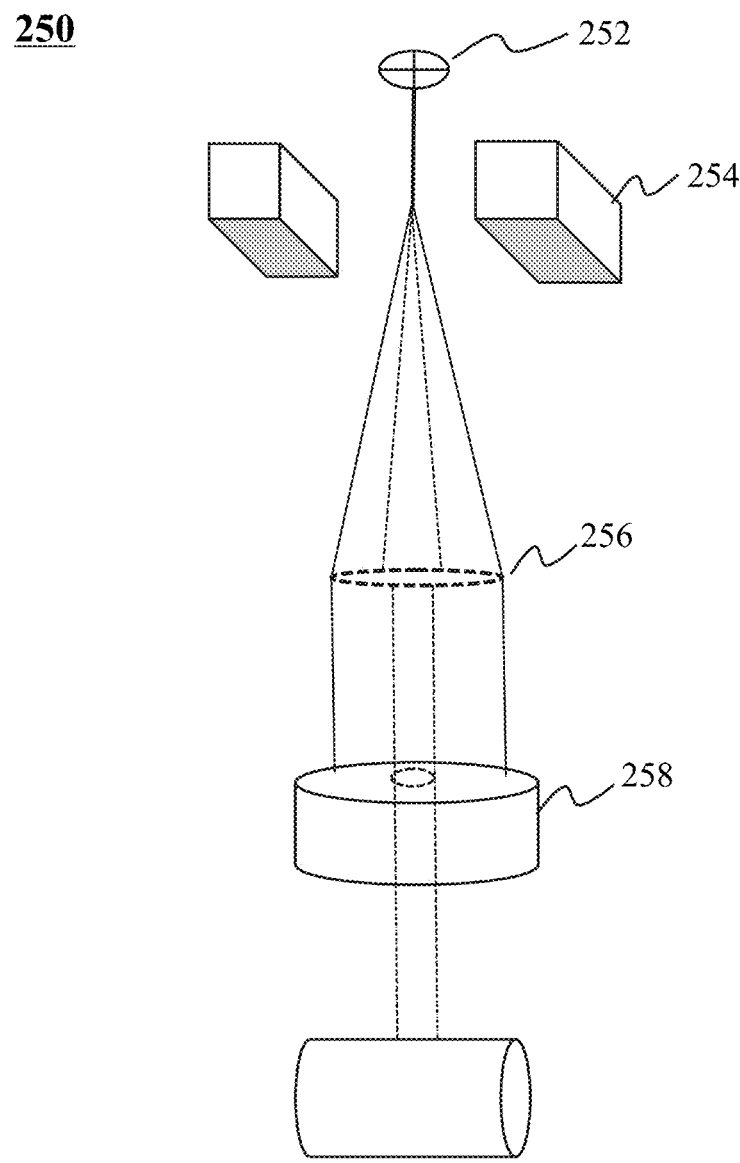
FIG. 2B is a schematic diagram illustrating exemplary components of a radiation therapy apparatus according to some embodiments of the present disclosure.

FIG. 2B is a schematic diagram illustrating exemplary components of a radiation therapy apparatus according to some embodiments of the present disclosure. As illustrated in FIG. 2B, the radiation therapy apparatus 250 may include a radiation beam generator 252, a beam control device 254, a target 256, and a treatment head 258. The radiation beam generator 252 may be configured to generate a radiation particle beam. For example, the radiation particle beam may include neutrons, electrons, hadrons (e.g., protons, ions), or other types of radiation particles. The descriptions in the following figures are provided with reference to a radiation particle beam of electrons. It can be understood that it is for illustration purposes and not intended to be limiting.

In some embodiments, the radiation beam generator 252 may include a linear accelerator (also referred to as "Linac"). The linear accelerator may be configured to accelerate electrons to form an electron beam with a certain energy level. For example, the electrons may be accelerated to form an electron beam with a high energy level. An electron beam with a high energy level refers to an electron beam with an energy greater than a threshold energy. The threshold energy may be, for example, 10 Mev, 20 Mev, 30 MeV, 40 MeV, 50 MeV, 100 MeV, 200 MeV, etc. Correspondingly, an electron beam with an energy lower than the threshold energy may be referred to as an electron beam with a low energy level.

The beam control device 254 may be configured to control the radiation particle beam generated by the radiation beam generator 252. For example, the radiation particle beam generated by the radiation beam generator 252 may be deflected, defocused, and/or focused by the beam control device 254. In some embodiments, the beam control device 254 may control the radiation particle beam to achieve a desired position, direction, spatial distribution, energy distribution, beam shape, etc. As used herein, a position may refer to a point or an area on a target (e.g., a tungsten plate, a molybdenum plate, etc.) onto which the electrons in the radiation particle beam collide. A direction may refer to a direction towards which the electrons in radiation particle beam emits. A spatial distribution may refer to a distribution of the electrons in the radiation particle beam in a three-dimensional space. An energy distribution may refer to a distribution of the energy of the electrons in the radiation particle beam. A beam shape may refer to a shape of a cross-section of the radiation particle beam.

In some embodiments, the beam control device 254 may include a deflection device and a beam profile modulator. The deflection device may be configured to deflect the radiation particle beam. Merely by way of example, the radiation beam generator 252 may emit an electron beam toward a direction, which may pass through the deflection device before reaching the subject. The moving trajectory (e.g., the position and the direction) of the electron beam may be altered by the deflection device when it passes through the deflection device. Exemplary deflection devices may include a microwave cavity, a magnet (e.g., a permanent magnet, an electromagnet, etc.), a magnetic lens, or the like, or any combination thereof. The beam profile modulator may be configured to control the beam shape of the radiation particle beam. Merely by way of example, the beam profile modulator may include one or more beam-limiting devices, such as a blocker, that may block a specific portion of the radiation particle beam.

The target 256 may produce radiation therapeutic beam for radiation treatment of the subject (e.g., the target region of the subject) when the accelerated electron beam collides on the target 256. For example, the electron beam emitted from the radiation beam generator 252 may be deflected onto the target 256 to generate X-rays at a high energy level according to the Bremsstrahlung effect. In some embodiments, the target 256 may be made of materials including aluminum, copper, silver, tungsten, or the like, or an alloy thereof, or any combination thereof.

The treatment head 258 may be located at a specific location and treat the subject using the radiation therapeutic beam from a specific angle. In some embodiments, one or more components of the beam control device 254 may be mounted on or integrated into the treatment head 258. For example, a beam profile modulator, such as a collimator, may be integrated into the treatment head 258. During a radiation treatment, a gantry supporting one or more components of the radiation therapy apparatus may be rotatable along an axis, and the treatment head 258 and the beam control device 254 may rotate with the gantry. For example, the gantry may rotate around the Z axis on the X-Y plane defined according to the coordinate system 160 as shown in FIG. 1.

In some embodiments, the radiation therapy apparatus may include a plurality of treatment heads, each of which may be equipped with a beam control device 254. A beam control device 254 (e.g., a multi-leaf collimator (MLC)) may be mounted on or integrated into the corresponding treatment head. In some embodiments, the radiation beam generator 252 and the beam control device 254 may be an integral assembly.

FIG. 3 is a schematic diagram illustrating exemplary hardware and/or software components of a computing device 300 according to some embodiments of the present disclosure. The computing device 300 may be used to implement any component of the radiation therapy system 100 as described herein. For example, the processing device 120 and/or the terminal 150 may be implemented on the computing device 300, respectively, via its hardware, software program, firmware, or a combination thereof. Although only one such computing device is shown, for convenience, the computer functions relating to the radiation therapy system 100 as described herein may be implemented in a distributed fashion on a number of similar platforms, to distribute the processing load. As illustrated in FIG. 3, the computing device 300 may include a processor 310, a storage 320, an input/output (I/O) 330, and a communication port 340.

The processor 310 may execute computer instructions (e.g., program code) and perform functions of the processing device 120 in accordance with techniques described herein. The computer instructions may include, for example, routines, programs, objects, components, data structures, procedures, modules, and functions, which perform particular functions described herein. For example, the processor 310 may process data obtained from the MRI apparatus 200, the terminal(s) 150, the storage device 140, and/or any other component of the radiation therapy system 100. In some embodiments, the processor 310 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 300. However, it should be noted that the computing device 300 in the present disclosure may also include multiple processors, thus operations and/or method operations that are performed by one processor as described in the present disclosure may also be jointly or separately performed by the multiple processors. For example, if in the present disclosure the processor of the computing device 300 executes both operation A and operation B, it should be understood that operation A and operation B may also be performed by two or more different processors jointly or separately in the computing device 300 (e.g., a first processor executes operation A and a second processor executes operation B, or the first and second processors jointly execute operations A and B).

The storage 320 may store data/information obtained from the MRI apparatus 200, the storage device 140, the terminal(s) 150, and/or any other component of the radiation therapy system 100. In some embodiments, the storage 320 may include a mass storage device, a removable storage device, a volatile read-and-write memory, a read-only memory (ROM), or the like, or any combination thereof. In some embodiments, the storage 320 may store one or more programs and/or instructions to perform exemplary methods described in the present disclosure. For example, the storage 320 may store a program for the processing device 120 to execute for generating an image of a region of interest (ROI) of the subject.

The I/O 330 may input and/or output signals, data, information, etc. In some embodiments, the I/O 330 may enable a user interaction with the processing device 120. In some embodiments, the I/O 330 may include an input device and an output device. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to another component (e.g., the processing device 120) via, for example, a bus, for further processing. Other types of the input device may include a cursor control device, such as a mouse, a trackball, or cursor direction keys, etc. The output device may include a display (e.g., a liquid crystal display (LCD), a light-emitting diode (LED)-based display, a flat panel display, a curved screen, a television device, a cathode ray tube (CRT), a touch screen), a speaker, a printer, or the like, or a combination thereof.

The communication port 340 may be connected to a network (e.g., the network 130) to facilitate data communications. The communication port 340 may establish connections between the processing device 120 and the MRI apparatus 200, the terminal(s) 150, and/or the storage device 140. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G), or the like, or a combination thereof. In some embodiments, the communication port 340 may be and/or include a standardized communication port, such as RS232, RS485, etc. In some embodiments, the communication port 340 may be a specially designed communication port. For example, the communication port 340 may be designed in accordance with the digital imaging and communications in medicine (DICOM) protocol.

Figure 4:
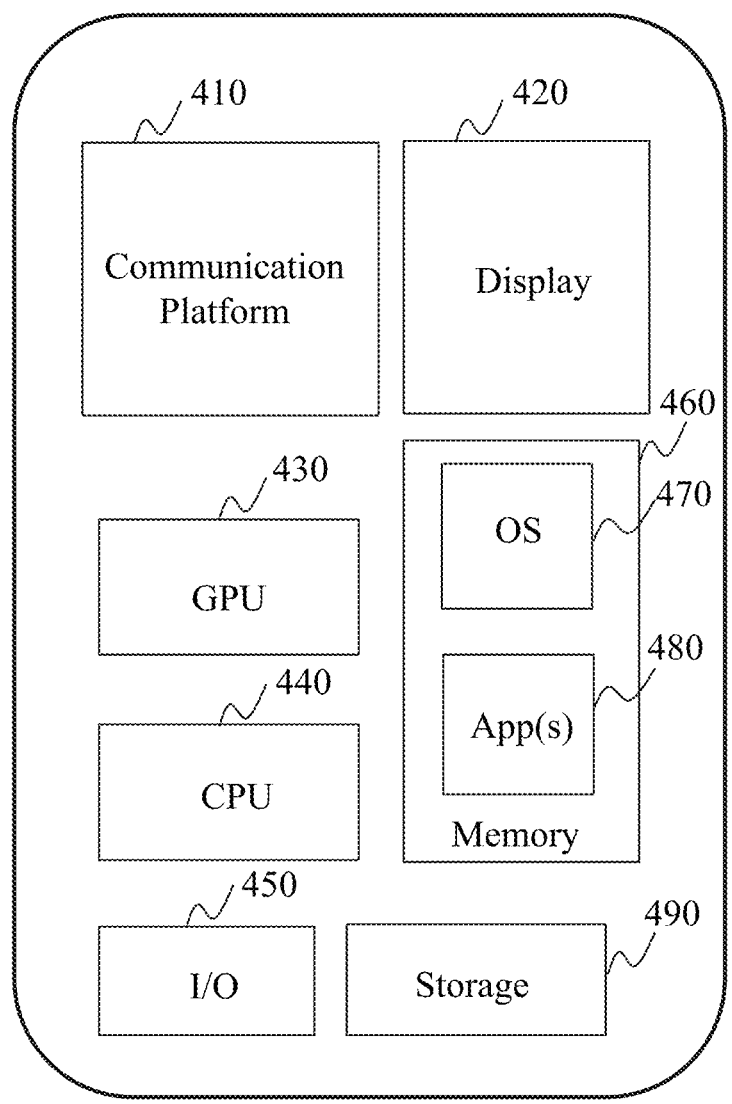
FIG. 4 is a schematic diagram illustrating exemplary hardware and/or software components of a mobile device according to some embodiments of the present disclosure.

FIG. 4 is a schematic diagram illustrating exemplary hardware and/or software components of a mobile device 400 according to some embodiments of the present disclosure. In some embodiments, one or more components (e.g., a terminal 150 and/or the processing device 120) of the radiation therapy system 100 may be implemented on the mobile device 400.

As illustrated in FIG. 4, the mobile device 400 may include a communication platform 410, a display 420, a graphics processing unit (GPU) 430, a central processing unit (CPU) 440, an I/O 450, a memory 460, and a storage 490. In some embodiments, any other suitable component, including but not limited to a system bus or a controller (not shown), may also be included in the mobile device 400. In some embodiments, a mobile operating system 470 (e.g., iOS™, Android™, Windows Phone™) and one or more applications 480 may be loaded into the memory 460 from the storage 490 in order to be executed by the CPU 440. The applications 480 may include a browser or any other suitable mobile apps for receiving and rendering information relating to the radiation therapy system 100. User interactions with the information stream may be achieved via the I/O 450 and provided to the processing device 120 and/or other components of the radiation therapy system 100 via the network 130.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 5:
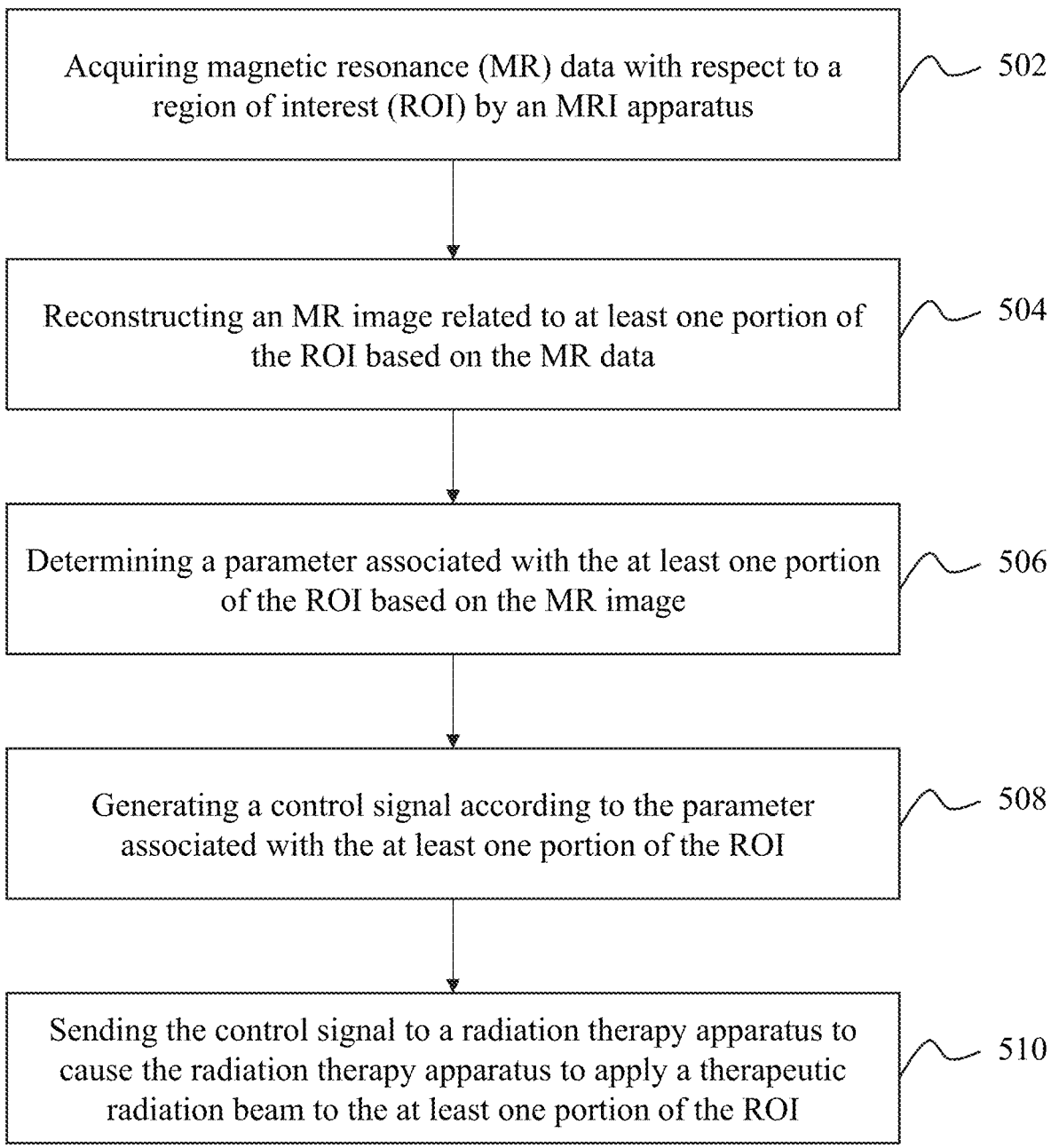
FIG. 5 is a flowchart illustrating an exemplary process for applying a therapeutic radiation in a radiation therapy system according to some embodiments of the present disclosure.

FIG. 5 is a flowchart of an exemplary process for applying a therapeutic radiation by a radiation therapy system according to some embodiments of the present disclosure. In some embodiments, one or more operations of the process 500 illustrated in FIG. 5 may be implemented in the radiation therapy system 100 illustrated in FIG. 1. For example, the process 500 illustrated in FIG. 5 may be stored in the storage device 140 in the form of instructions, and invoked and/or executed by the one or more processing devices 120 illustrated in FIG. 1. For illustration purposes, the implement of the process 500 in the one or more processing devices 120 is described herein as an example. It should be noted that the process 500 can also be similarly implemented in the terminal device 150.

In 502, the one or more processing devices 120 may acquire magnetic resonance (MR) data with respect to a region of interest (ROI) by an MRI apparatus. The MR data may be MR signals received by an RF coil of the MRI apparatus (e.g., the MRI apparatus 200) from a subject.

In some embodiments, an ROI may refer to a region, e.g., a lesion, in a subject. For example, the ROI may be a region associated with a tumor of the subject. In some embodiments, the ROI may be a specific portion of the body, a specific organ, or specific tissue of the subject, such as the head, the brain, the neck, the body, shoulders, arms, the thorax, the heart, the stomach, blood vessels, soft tissue, knee, feet, etc., of the subject.

In 504, the one or more processing devices 120 may reconstruct an MR image of the ROI based on the MR data. The MR image may reflect a distribution of atomic nuclei inside the subject based on the MR data. Image reconstruction techniques of various types may be employed for reconstructing the MR image. Exemplary image reconstruction techniques may include Fourier reconstruction, constrained image reconstruction, regularized image reconstruction in parallel MRI, or the like, or a variation thereof, or any combination thereof.

In some embodiments, the MR image may be used to determine a therapeutic radiation beam to be applied to a target region (e.g., at least one portion of the ROI). For example, the one or more processing devices 120 may determine the position of the at least one portion of the ROI and/or the dose of radiation to be delivered according to the MR image.

In some embodiments, it may take a long time (e.g., several minutes) to reconstruct an MR image of the ROI. It may be difficult to reconstruct an MR image of the ROI in real time during the radiation treatment if the ROI has a large size. In some embodiments, in order to generate the MR image of the ROI during a relative short time period (e.g., several seconds), the one or more processing devices 120 may reconstruct an MR image of the at least one portion of the ROI. The MR image of the entire ROI (also referred to as primary MR image) may be reconstructed in advance (e.g., one day, two hours, half an hour, etc., before the radiation treatment). The processing device 120 may obtain MR data of the at least one portion of the ROI acquired by the MRI apparatus, and reconstruct an MR image of the at least one portion of the ROI during the radiation treatment (e.g., right before the therapeutic radiation beam is applied on the at least one portion of the ROI). The processing devices 120 may combine MR image of the at least one portion of the ROI with the primary MR image. For example, the one or more processing devices 120 may use the MR image of the at least one portion of the ROI to replace a corresponding portion in the primary MR image. In this way, the primary MR image may be updated in a relatively short time period during the radiation treatment.

In 506, the one or more processing devices 120 may determine a parameter associated with the at least one portion of the ROI based on the MR image. In some embodiments, the parameter associated with the at least one portion of the ROI may include a size of a cross section of a lesion (e.g., a tumor) corresponding to the at least one portion of the ROI. In some embodiments, the parameter associated with the at least one portion of the ROI may indicate a shape of the cross section of the lesion.

In 508, the one or more processing devices 120 may generate a control signal according to the parameter associated with the at least one portion of the ROI. The control signal may be dynamically adjusted based on a plurality of MR images taken at different time points during the radiation treatment. In some embodiments, the control signal may include parameters associated with the therapeutic radiation beam applied on the tumor. For example, the control signal may include the dosage of an X-ray beam, a duration of the therapeutic radiation beam applied on the at least one portion of the ROI, etc. As another example, the control signal may include parameters of an MLC that shapes the therapeutic radiation beam projected to the at least one portion of the ROI. In some embodiments, the control signal may include parameters associated with movements of one or more components of a radiation therapy apparatus (e.g., the radiation therapy apparatus 250). For example, the control signal may include a parameter associated with one or more positions of a radiation source of the radiation therapy apparatus (e.g., the target 256 of the radiation therapy apparatus 250). As another example, the control signal may include a parameter associated with a height and/or a position of a treatment table of the radiation therapy apparatus for properly positioning a patient so that the target region (e.g., a region corresponding to a lesion) in the patient may properly receive the therapeutic radiation beam from the radiation therapy apparatus.

In 510, the one or more processing devices 120 may send the control signal to the radiation therapy apparatus to cause the radiation therapy apparatus to apply the therapeutic radiation beam to the at least one portion of the ROI. During the therapeutic radiation, the radiation source of the radiation therapy apparatus may rotate around a rotation axis. The dosage of the X-ray beam, a duration of the therapeutic radiation beam applied to the at least one portion of the ROI, the shape of the MLC, and/or the position of the treatment table may be adjusted according to the control signal.

In some embodiments, as described above, the target region (e.g., the at least one portion of the ROI) may be determined according to the image data acquired from the MRI apparatus during the radiation treatment. Then the therapeutic radiation beam may be generated and delivered by the radiation therapy apparatus to the target region. The dosage of the radiation therapeutic beam and/or the position of the target region may be determined almost in real-time with the assistance of the MRI apparatus.

It should be noted that the above description is merely provided for the purposes of illustration, and not intended to limit the scope of the present disclosure. For persons having ordinary skills in the art, multiple variations or modifications may be made under the teachings of the present disclosure. For example, the primary MR image may be obtained from a storage device in the radiation therapy system 100, such as the storage device 140. As another example, the parameter associated with the at least one portion of the ROI determined based on the MR image may also include a position of the at least one portion of the ROI in a coordinate system (e.g., the coordinate system 160 as illustrated in FIG. 1). However, those variations and modifications do not depart from the scope of the present disclosure.

Figure 6:
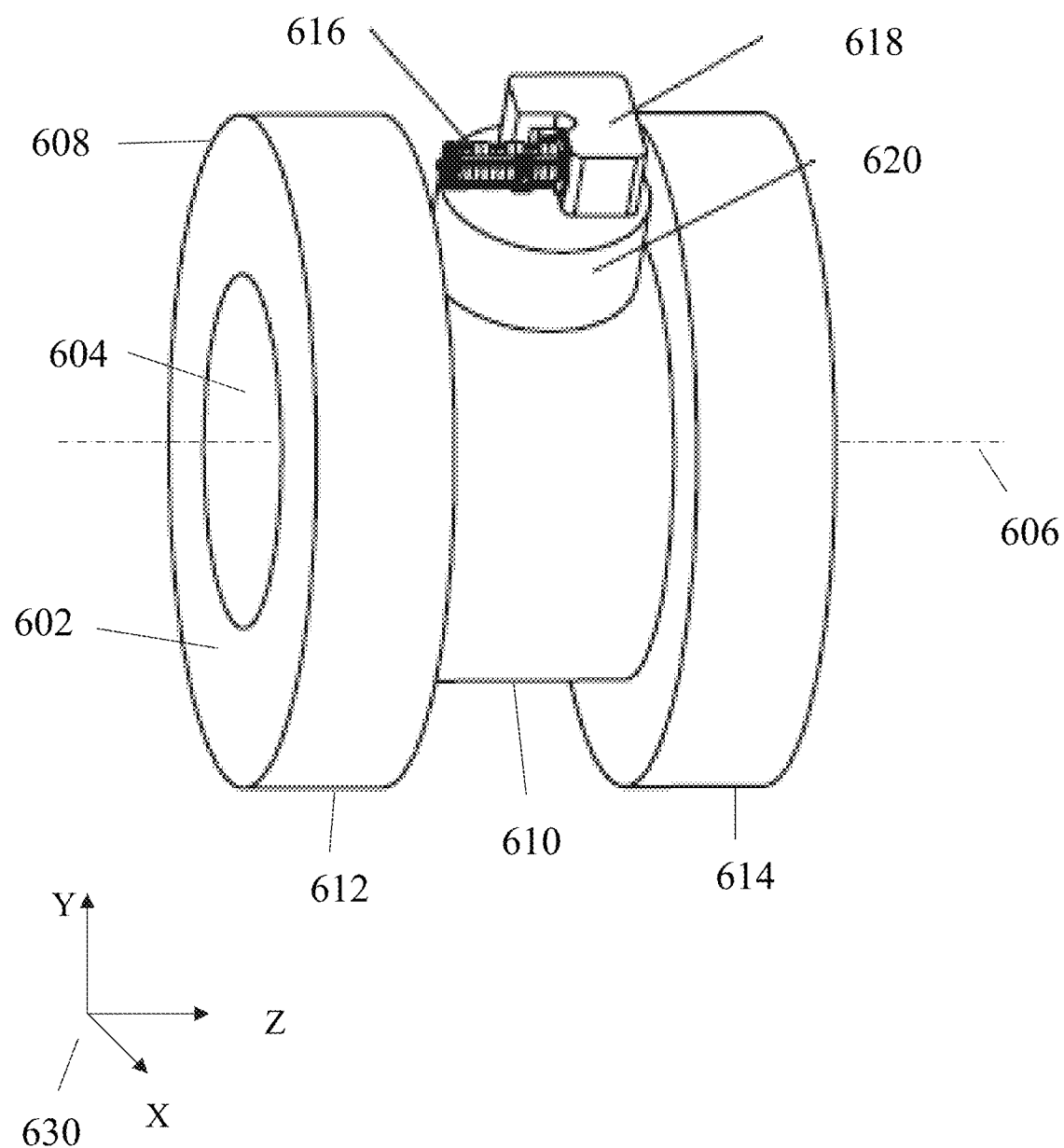
FIG. 6 illustrates a perspective view of an exemplary therapeutic apparatus according to some embodiments of the present disclosure.

FIG. 6 illustrates a perspective view of an exemplary therapeutic apparatus according to some embodiments of the present disclosure. The therapeutic apparatus 600 may include an MRI apparatus configured to generate MR data of an ROI of a subject and a radiation therapy apparatus configured to apply a therapeutic radiation beam to at least one portion of the ROI based on an MR image reconstructed based on the MR data.

In some embodiments, the MRI apparatus may be or include a permanent magnet MRI scanner, a superconducting electromagnet MRI scanner, or a resistive electromagnet MRI scanner, etc., according to types of a magnetic body of the MRI apparatus. In some embodiments, the MRI apparatus may be or include a high-field MRI scanner, a mid-field MRI scanner, and a low-field MRI scanner, etc., according to an intensity of a magnetic field generated by the magnetic body of the MRI apparatus. In some embodiments, the MRI apparatus may be of a closed-bore (cylindrical) type, an open-bore type, or the like. The MRI apparatus may include a magnetic body 602 and a bore 604.

The magnetic body 602 may have a shape of an annulus around an axis 606, which is parallel to the Z direction of the coordinate system 630. An inner surface of the magnetic body 602 may form the bore 604. The magnetic body 602 may generate a magnetic field. The magnetic body 604 may be of various types including, for example, a permanent magnet, a superconducting electromagnet, a resistive electromagnet, etc. The following descriptions are provided that the magnetic body 604 may be a superconducting electromagnet. It is understood that it is merely for illustration purposes, and not intended to be limiting.

In some embodiments, the magnetic body 602 may include a plurality of main magnetic coils and a plurality of shielding magnetic coils. The plurality of main magnetic coils may be arranged around the axis 606. The plurality of main magnetic coils may generate a uniform main magnetic field (e.g., a static magnetic field $B_0$) within a specific region (e.g., the bore 604) when the plurality of main magnetic coils 602 carry an electric current.

The plurality of shielding magnetic coils may shield the magnetic field generated by the plurality of main magnetic coils in a region outside the MRI apparatus. In some embodiments, the plurality of shielding magnetic coils may carry an electric current along a direction that is opposed to the direction of the electric current on the plurality of main magnetic coils. A magnetic field generated by the plurality of shielding magnetic coils may reduce or cancel the magnetic field generated by the plurality of main magnetic coils in the region outside the MRI apparatus. In some embodiments, the plurality of shielding magnetic coils may be annular coils arranged along the axis 606, coaxially with the plurality of main magnetic coils. In some embodiments, the plurality of shielding magnetic coils may be of at a larger radius from the axis 606 than the plurality of main magnetic coils.

In some embodiments, the magnetic body 602 may further include a cryostat 608. In some embodiments, the plurality of main magnetic coils and the plurality of shielding magnetic coils may be accommodated in the cryostat 608. The cryostat 608 may contain a coolant, for example, liquid helium. The plurality of main magnetic coils and the plurality of shielding magnetic coils may be immerged in the coolant in the cryostat 608. The coolant may maintain the plurality of main magnetic coils and the plurality of shielding magnetic coils at a low temperature (e.g., 4.2 K) such that the plurality of main magnetic coils and the plurality of shielding magnetic coils may maintain a superconducting state. The cryostat 608 may have a shape of an annulus around the axis 606.

The MRI apparatus may further include one or more gradient coils (not shown). The one or more gradient coils may generate magnetic field gradients to be superposed on the main magnetic field $B_0$ in the X, Y, and/or Z directions. In some embodiments, the one or more gradient coils may include at least one X coil, at least one Y coil, and/or at least one Z coil, etc. An X coil may be energized to generate a gradient field in the X direction. A Y coil may be energized to generate a gradient field in the Y direction. A Z coil may be energized to generate a gradient field in the Z direction. Merely by way of example, the at least one Z coil may be designed based on a circular (Maxwell) coil, and the at least one X coil and the at least one Y coil may be designed based on a saddle (Golay) coil. In some embodiments, the one or more gradient coils may be split gradient coils.

In some embodiments, the gradient magnetic fields may include a slice-selection gradient field corresponding to the Z direction, a phase encoding (PE) gradient field corresponding to the Y direction, a readout (RO) gradient field corresponding to the X direction, etc. The gradient magnetic fields in different directions may be used to encode spatial information of MR signals. In some embodiments, the gradient magnetic fields may also be used to perform at least one function of flow encoding, flow compensation, flow dephasing, or the like, or any combination thereof.

The one or more gradient coils may be located in the bore 602. In some embodiments, the one or more gradient coils may be arranged on or close to (e.g., having a distance of 1 centimeter, 2 centimeters, 5 centimeters, etc., to the surface of the bore 604) the surface of the bore 604.

The cryostat 608 may include an outer wall and an inner wall. The outer wall may have a larger radius than the inner wall. In some embodiments, as illustrated in FIG. 6, a recess 610 may be set between the outer wall and the inner wall. The recess 610 may have an annular opening (e.g., an annular recess or an annular slot) formed on the outer wall of the cryostat 608. A width of the recess 610 (i.e., the size of the recess 610 in the Z direction) may be of a same or different values at different positions along the circumferential direction. In some embodiments, the width of the recess 610 may be of a same value at different positions along the circumferential direction. In some embodiments, the width of the recess 610 may relate to size(s) of one or more components of the radiation therapy apparatus. In some embodiments, the width of the recess 610 may relate to a size of a treatment head of the radiation therapy apparatus. In some embodiments, the treatment head 620 may have a shape of a cylinder. The width of the recess 610 may be larger than or equal to a diameter of a flat surface of the treatment head 620. The recess 610 may have a depth (i.e., the thickness of the annulus in the radial direction) of a specific value. In some embodiments, the depth of the recess 610 may be smaller than a thickness of the cryostat 608 (i.e., distance between the inner wall and the outer wall of the cryostat 608). In some embodiments, the depth of the recess 610 may be equal to the thickness of the cryostat 608. Two chambers 612 and 614 may be formed at both ends of the cryostat 608, respectively, due to the recess 610. In some embodiments, the plurality of shielding coils and the plurality of the main magnetic coils may be arranged in the two chambers.

Alternatively, the recess 610 may have an opening (e.g., a poroid recess or a hole) formed on the outer wall of the cryostat 608. The recess 610 may have any suitable shape in its cross-section formed when the recess 610 is view along the radial direction of the MRI apparatus. The radial direction of the MRI apparatus may refer to radial direction of a cylindrical body of the MRI apparatus. For example, the recess 610 may have a shape of a square, a rectangle, a circle, an oval, etc., in its cross-section. In some embodiments, the recess 610 may have a shape of a circle in its cross-section. In some embodiments, the recess 610 may have a depth (i.e., the length of the poroid recess in the radial direction) of a specific value. In some embodiments, the depth of the recess 610 may be smaller than a thickness of the cryostat 608 (i.e., distance between the inner wall and the outer wall of the cryostat 608). In some embodiments, the depth of the recess 610 may be equal to the thickness of the cryostat 608 (i.e., the recess 610 may be a through-hole on the cryostat 608). The through-hole may extend through the cryostat 608 along the radial direction of the MRI apparatus.

The recess 610 may be configured to accommodate at least in part of one or more components of the radiation therapy apparatus. The following descriptions are provided, unless otherwise stated expressly, with reference to an annular recess set on the outer wall of the cryostat 608. It shall be understood that it is merely for illustration purposes, and not intended to be limiting. As shown in FIG. 6, the recess 610 may be configured to accommodate a linear accelerator 616, a deflection device 618, and a treatment head 620 of the radiation therapy apparatus. Detailed descriptions regarding the recess 610 may be described elsewhere in the present disclosure. See, for example, FIG. 7 and the descriptions thereof.

The linear accelerator 616 may accelerate electrons to form an electron beam with a certain energy level. In some embodiments, the linear accelerator 616 may accelerate electrons using microwave technology. In some embodiments, the linear accelerator 616 may be operably coupled to a microwave device (not shown in the figure). The microwave device may be configured to accelerate the electrons in the linear accelerator 616. In some embodiments, the linear accelerator 616 may be operably coupled to the microwave device through a rotation waveguide. The rotation waveguide may enable the microwave device to stand stationary relative to the MRI apparatus when the linear accelerator 616 rotates around the axis 606 during the radiation treatment of the subject. In some embodiments, the microwave device may also rotate around the axis 606 along with the linear accelerator 616 during the radiation treatment of the subject.

In some embodiments, the linear accelerator 616 may be located at least in part in the recess 616. In some embodiments, a length direction of the linear accelerator 616 may be parallel with the axis 606. More specifically, the linear accelerator 616 may include an accelerating tube. The accelerating tube may provide a linear path for accelerating the electrons. An axis of the accelerating tube may be parallel to the axis 606 (or the Z direction). The plurality of main magnetic coils and the plurality of shielding magnetic coils may generate a magnetic field that is parallel or substantially parallel to the axis 606 (also referred to as "parallel magnetic field") in a region where the linear accelerator 616 is located. It shall be appreciated that the parallel magnetic field may pose least influence to the electron beam in the accelerating tube of the linear accelerator 616. Thus, the linear accelerator 616 may not need a magnetic shielding for shielding the magnetic field in the accelerating tube.

In some embodiments, the linear accelerator 616 may be located on a platform. The platform may intersect with a radial plane of the MRI apparatus. As used herein, a radial plane of the MRI apparatus refers to a plane constituted by radial directions of the MRI apparatus that passes through a same point on the axis 606. Since the main magnetic coils are arranged around the axis 606, the radial plane of the MRI apparatus may be parallel to the X-Y plane with reference to the coordinate system 630. An intersection angle between the platform and the radial plane may be 30 degrees, 50 degrees, 70 degrees, 90 degrees, 120 degrees, 150 degrees, etc. In some embodiments, the intersection angle between the platform and the radial plane may be substantially 90 degrees (i.e., the platform may be substantially perpendicular to the radial plane of the MRI apparatus). In some embodiments, the platform may be implemented by the treatment head 620. Merely for illustration purposes, as illustrated in FIG. 6, the treatment head 620 may have a shape of a cylinder. A flat surface of the cylinder having a larger distance to the axis 606 may serve as the platform. The linear accelerator 616 may be fixed on the flat surface. The flat surface may have a shape of a circle. A center of the circle may be designated as the center of the platform.

In some embodiments, the linear accelerator 616 (e.g., an accelerating tube of the linear accelerator 616) may be at least partially surrounded by a radiation shielding component (not shown in FIG. 6). The radiation shielding component may protect the subject and/or one or more components of the MRI apparatus from the radiation produced by the linear accelerator 616. In some embodiments, the radiation shielding component may provide a cavity coaxial with the longitudinal direction of the linear accelerator 616, with at least one end being open to let through the electron beam emitted from the linear accelerator 616. In some embodiments, the radiation shielding component may have an annular structure surrounding the linear accelerator 616. A length of the radiation shielding component in the Z direction may be equal to or greater than a length of the linear accelerator 616.

The radiation shielding component may be made of a material that absorbs the radiation produced by the radiation beam of the linear accelerator 616 so as to provide radiation shielding for the subject and/or the one or more components of the MRI apparatus. Exemplary materials that absorb radiation may include a material for absorbing a photon ray and/or a material for absorbing a neutron ray. The material for absorbing a photon ray may include steel, aluminum, lead, tungsten, etc., or an alloy thereof, or a combination thereof. The material for absorbing a neutron ray may include boron, graphite, etc., or an alloy thereof, or a combination thereof.

The deflection device 618 may be configured to deflect the electron beam emitted from the linear accelerator 616 towards a target. Exemplary deflection devices may include a microwave cavity, a deflection magnet, a magnetic lens, or the like, or any combination thereof. In some embodiments, the deflection device 618 may include at least one deflection magnet. The at least one deflection magnet may be a permanent magnet, an electromagnet, etc. In some embodiments, the deflection device 618 may be implemented by a permanent magnet if the energy level of the electron beam emitted from the linear accelerator 616 is fixed. In some embodiments, the deflection device 618 may be implemented by an electromagnet if the energy level of the electron beam emitted from the linear accelerator 616 varies. For example, the energy level of the electron beam emitted from the linear accelerator 616 may range from 6 Mev to 10 Mev, and the deflection device 618 may be implemented by an electromagnet so as to deflect the electron beam of different energy levels to the target.

In some embodiments, the deflection device 618 may include an inlet and an outlet. In some embodiments, the inlet of the deflection device 618 may be aligned with an exit window of the linear accelerator 616 (i.e., an outlet of the linear accelerator 616). The electron beam may pass through the deflection device 618 in a moving trajectory from the inlet to the outlet of the deflection device 618.

In this process, the deflection device 618 may deflect the electron beam by a deflection angle. The deflection angle may be any suitable angle that satisfy a preset condition. In some embodiments, the preset condition may be that an intersection angle between a direction of the electron beam and a direction of the magnetic field at the outlet of the deflection device 618 is not equal to 0 degrees or 180 degrees. In some embodiments, the preset condition may be that the intersection angle between the direction of the electron beam and the direction of the magnetic field at the outlet of the deflection device 618 is in a certain range (e.g., 15 degrees to 165 degrees and 195 degrees to 345 degrees, 30 degrees to 150 degrees and 210 degrees to 330 degrees, etc.). For example, the deflection angle may be 90 degrees, 120 degrees, 150 degrees, 200 degrees, 250 degrees, 270, degrees, etc. In some embodiments, the deflection angle may be 270 degrees. Taking a deflection angle of 270 degrees as an example, the electron beam emitted from the linear accelerator 616 may enter the inlet of the deflection device 618 along a positive direction of the Z axis, and emit out of the deflection device 618 from its outlet along a positive direction of the X axis.

In some embodiments, the trajectory of the electron beam in the deflection device 618 may be on a plane intersecting with the radial plane of the MRI apparatus. An intersection angle between the plane and the radial plane of the MRI apparatus may be 30 degrees, 50 degrees, 70 degrees, 90 degrees, 120 degrees, 150 degrees, etc. In some embodiments, the intersection angle between the plane and the radial plane may be substantially 90 degrees (i.e., the plane may be substantially perpendicular to the radial plane of the MRI apparatus).

In some embodiments, the plane on which the trajectory of the electron beam in the deflection device 618 is may be parallel to the platform on which the linear accelerator 616 is located. The trajectory of the electron beam on the plane may be referred to as a first portion of a moving trajectory of the electron beam. A distance between the plane on which the first portion of the moving trajectory of the electron beam is and the platform on which the linear accelerator 616 is located may be equal to a radius of the accelerating tube of the linear accelerator 616.

In some embodiments, the deflection device 618 may include a deflection channel. The electron beam may be deflected by the deflection angle in the deflection channel. In some embodiments, the deflection device 618 may further include a magnetic shielding component for shielding the magnetic field generated by the plurality of main magnetic coils and the plurality of shielding coils in the deflection channel. In some embodiments, the magnetic shielding component may include one or more magnetic shielding structures that are made of high magnetic susceptibility and/or permeability materials.

In some embodiments, the deflection device 618 may be configured to correct dispersion of the electrons in the electron beam. In some embodiments, one or more parameters of the deflection device 618 may be designed so as to correct the dispersion of the electrons in the electron beam. The one or more parameters may relate to the size, structure, material and/or magnetic property of at least one deflection magnet of the deflection device 618.

In some embodiments, the deflection device 618 may also be placed on the flat surface of the treatment head 620 having a larger distance to the axis 606. The deflection device 618 may be connected to the linear accelerator 616. For example, the inlet of the deflection device 618 may be align to and connected to the exit window of the linear accelerator 616. Detailed descriptions regarding the deflection device 618 may be described elsewhere in the present disclosure. See, for example, FIG. 8 and the descriptions thereof.

After the electron beam is emitted out of the deflection device 618, the electron beam may be within the magnetic field generated by the plurality of main magnetic coils and the plurality of shielding coils. Since the intersection angle between the direction of the electron beam and the direction of the magnetic field at the outlet of the deflection device 618 is not equal to 0 degrees or 180 degrees, a Lorentz force may be enforced on the electron beam, such that the electron beam may be deflected out of the plane in a second portion of the moving trajectory of the electron beam, and collides onto the target.

The target may produce a radiation therapeutic beam for radiation treatment of the subject (e.g., the at least portion of the ROI of the subject) when the accelerated electron beam collide onto the target. For example, the electron beam emitted from the linear accelerator 616 may be deflected onto the target to generate X-rays at a high energy level according to the Bremsstrahlung effect. In some embodiments, the target may be made of a material including aluminum, copper, silver, tungsten, or the like, or an alloy thereof, or any combination thereof. Alternatively, the target may be made of a composite material including tungsten and copper, tungsten and silver, tungsten and aluminum, or the like, or an alloy thereof, or any combination thereof. In some embodiments, the target may be a circular plate having a relatively small thickness (e.g., several micrometers to dozens of micrometers).

The radiation beam from the target may pass through the treatment head 620. The treatment head 620 may be configured to deliver radiation therapeutic beam to a target region of the subject from a specific angle. The treatment head 620 may include a collimator (not shown in the figure) to reshape the radiation therapeutic beam. For example, the collimator may adjust an irradiating shape, an irradiating area, etc., of the radiation therapeutic beam by blocking a specific portion of the radiation therapeutic beam. In some embodiments, the collimator may include a primary collimator, a flattening filter, and at least one secondary collimator. In some embodiments, the collimator may be an MLC. The MLC may include a plurality of individual leaves moving independently in and out of the path of the radiation therapeutic beam so as to block a specific portion of the radiation therapeutic beam. The shape of the radiation therapeutic beam may vary when the plurality of individual leaves move in and out, forming different slots that approximates a cross-sectional view of the target region (e.g., the at least one portion of the ROI) viewed along the radiation therapeutic beam. In some embodiments, the MLC may include one or more layers of leaves. For example, the MLC may have only one layer of leaves and the height of the MLC along the axis of the radiation therapeutic beam may be between 7 and 10 centimeters. As another example, the MLC may include two layers and the height of the MLC may be at least 15 centimeters. The leaves of the MLC may be made of at least one high atomic numbered material (e.g., tungsten).

The treatment head 620 may be placed at the bottom of the recess 610. In some embodiments, a movable component may be set at the bottom of the recess 610. The treatment head 620 may be movable in the recess 610 via the movable component. In some embodiments, the movable component may include a sliding rail, a rolling bearing, etc.

In some embodiments, one or more of the linear accelerator 616, the deflection device 618, and the target may stay fixed relative to the treatment head 620, thus rotating together with the treatment head 620 in the recess 610 around the axis 606 during the radiation treatment of the subject. In some embodiments, the treatment head 620 may be connected to the gantry. For example, the treatment head 620 be connected to the gantry via a physical structure (e.g., mechanical structures such as one or more rods, one or more plates, not shown), a glue, or the like, or a combination thereof. The gantry may be capable of rotating around the axis 606. The components of the radiation therapy apparatus may rotate around the axis 606 along with the gantry during the radiation treatment of the subject, and thus may enable the radiation therapeutic beam to be emitted to the target region of the subject from any one of circumferential positions along the circumference of or defined by the therapeutic apparatus 600.

It should be noted that the above description is merely provided for the purposes of illustration, and not intended to limit the scope of the present disclosure. For persons having ordinary skills in the art, multiple variations or modification may be made under the teaching of the present disclosure. In some embodiments, one or more of the linear accelerator 616, the deflection device 618, and the target may stay fixed relative to the treatment head 620. The treatment head 620 may be fixed relative to the cryostat 608 in the case that the one or more components of the radiation therapy apparatus are placed in the poroid recess. The magnetic body 602 may be connected to the gantry. The gantry may be capable of rotating around the axis 606. One or more components of the MRI apparatus and the radiation therapy apparatus may rotate around the axis 606 along with the gantry during the radiation treatment of the subject, and thus may enable the radiation therapeutic beam to be emitted to the target region of the subject from any one of circumferential positions along the circumference of or defined by the therapeutic apparatus 600. However, those variations and modifications do not depart from the scope of the present disclosure.

Figure 7:
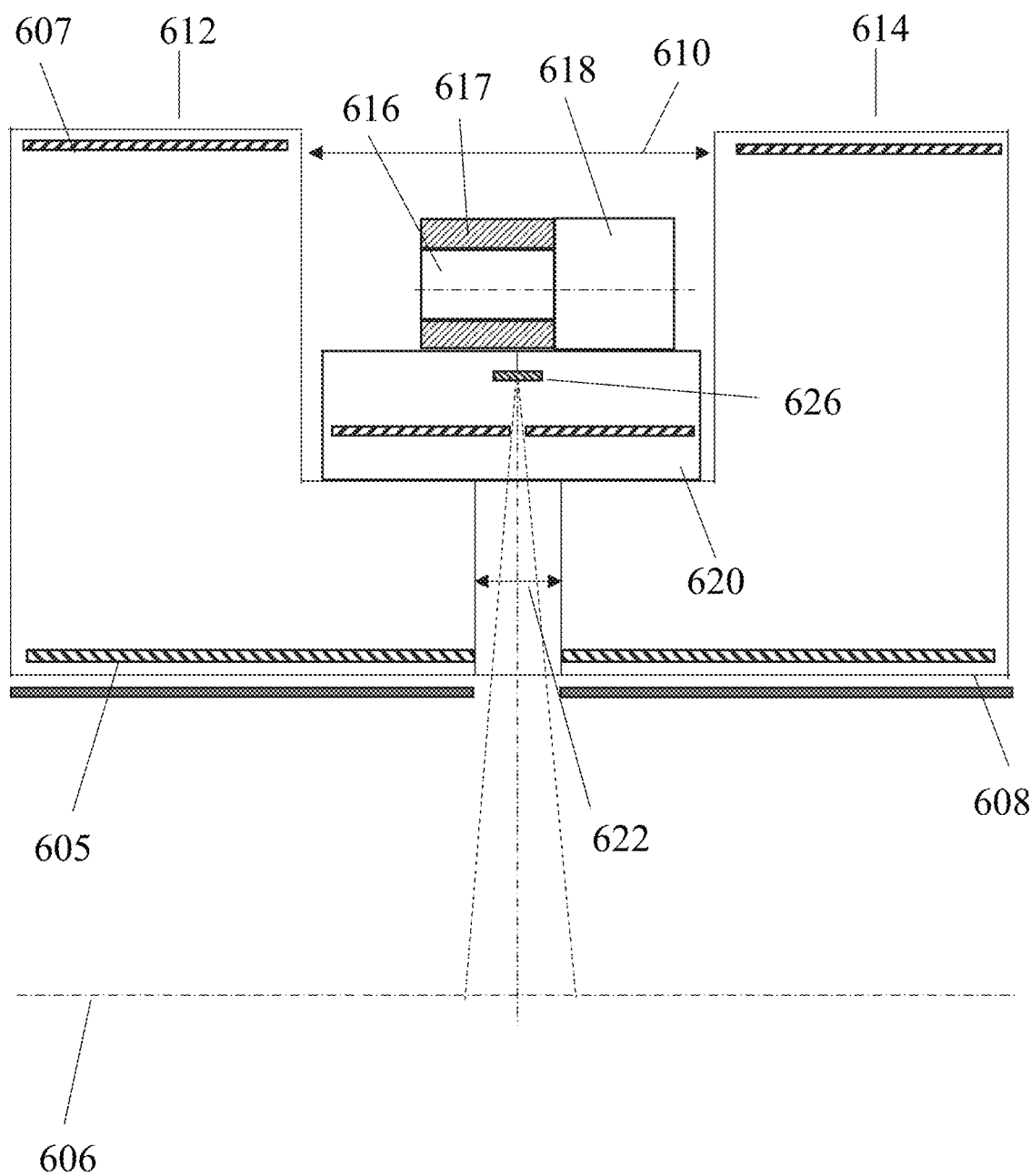
FIG. 7 illustrates a cross-sectional view of an upper portion of a therapeutic apparatus according to some embodiments of the present disclosure.

FIG. 7 illustrates a cross-sectional view of an upper portion of a therapeutic apparatus according to some embodiments of the present disclosure. The cross-sectional view may be formed by viewing the therapeutic apparatus 600 along a negative direction of the X axis with reference to the coordinate 630 in FIG. 6. The structure of the MRI apparatus of the therapeutic apparatus 600 may be cylindrically symmetrical around the axis 606.

The therapeutic apparatus 600 may include an MRI apparatus and a radiation therapy apparatus. The MRI apparatus may include a cryostat 608, a plurality of main magnetic coils 605, and a plurality of shielding magnetic coils 607. The radiation therapy apparatus may include a linear accelerator 616, a radiation shielding component 617, a deflection device 618, a target 626, and a treatment head 620. The components of the MRI apparatus and the radiation therapy apparatus of the therapeutic apparatus 600 are disclosed in FIG. 6, and the descriptions thereof are not repeated here.

As illustrated in FIG. 7, the cryostat 608 may have a recess 610 formed on the outer wall of the cryostat 608. In some embodiments, the recess 610 may have a shape of an annulus along a circumferential direction of the cryostat 608. In some embodiments, the recess 610 may have a shape of a through-hole along a radial direction of the MRI apparatus. The linear accelerator 616 and the deflection device 618 may be set on the treatment head 620.

Two chambers 612 and 614 may be formed at both ends of the cryostat 608, respectively, in the longitudinal direction of the cryostat 608 (i.e., the Z direction) due to the configuration of the recess 610. In some embodiments, the plurality of shielding coils 607 including a first part of plurality of shielding coils and a second part of plurality of shielding coils may be arranged in the two chambers 612 and 614, respectively. For example, the plurality of shielding coils 607 may include two shielding coils. The two shielding coils may be arranged in the two chambers 612 and 614, respectively. The plurality of main magnetic coils 605 including a first part of plurality of main magnetic coils and a second part of plurality of main magnetic coils may also be arranged in the two chambers 612 and 614, respectively. In some embodiments, the first part of plurality of shielding coils and a second part of plurality of shielding coils may be arranged close to the outer wall the two chambers 612 and 614, respectively. The first part of plurality of main magnetic coils and a second part of plurality of main magnetic coils may be arranged close to the inner wall of the two chambers 612 and 614, respectively.

One or more components of the radiation therapy apparatus, including the linear accelerator 616, the deflection device 618, and the treatment head 620, may be disposed between the two neighboring shielding coils of the plurality of shielding coils. The two neighboring shielding coils may belong to the first part of plurality of shielding coils and the second part of plurality of shielding coils, respectively.

In some embodiments, the one or more components of the radiation therapy apparatus may be movable in the recess 610 around the subject in the bore 604, and deliver the radiation therapeutic beam to the subject through a groove 622 set at the bottom of the recess 610. In some embodiments, a width of the groove 622 may be smaller than the diameter of the treatment head 620. In some embodiments, the groove 622 may include one or more portions along the circumferential direction. Merely by way of example, the groove 622 may include two or more arc-shaped portions along the circumferential direction. A neck structure may be formed between each two neighboring arc-shaped portions of the two or more arc-shaped portions of the groove 622. The neck structure may be configured to establish a fluid communication between the two chambers 612 and 614.

In some embodiments, the one or more gradient coils (not shown in the figure) may be split gradient coils. Each split gradient coil may include at least one gradient coil. In some embodiments, a split gradient coil may have an annular structure or a portion of an annulus around the axis 606. In some embodiments, the split gradient coils may be spaced apart from each other along the Z direction with reference to the coordinate system 630 as illustrated in FIG. 6. Merely for illustration purposes, the one or more gradient coils may be configured as two split gradient coils around the axis 606. The two split gradient coils may be spaced apart along the Z direction, thus forming an annular gap. The annular gap may be aligned with the groove 622 in a radial direction so as to let through the radiation therapeutic beam.

In a case that the depth of the recess 610 is equal to the thickness of the cryostat 608, the cryostat 608 may be divided into two chambers independent from each other. The plurality of shielding coils and the plurality of the main magnetic coils may be arranged in the two independent chambers. In some embodiments, the one or more components of the radiation therapy apparatus, including the linear accelerator 616, the deflection device 618, and the treatment head 620, may be placed on a circular supporting structure (e.g., a sliding rail) set on at least one independent chamber such that one or more of the components of the radiation therapy apparatus may be at least in part disposed between the two independent chambers 612 and 614. In some embodiments, the one or more components of the radiation therapy apparatus may be movable around the subject in the bore 604 along the circular supporting structure.

Figure 8:
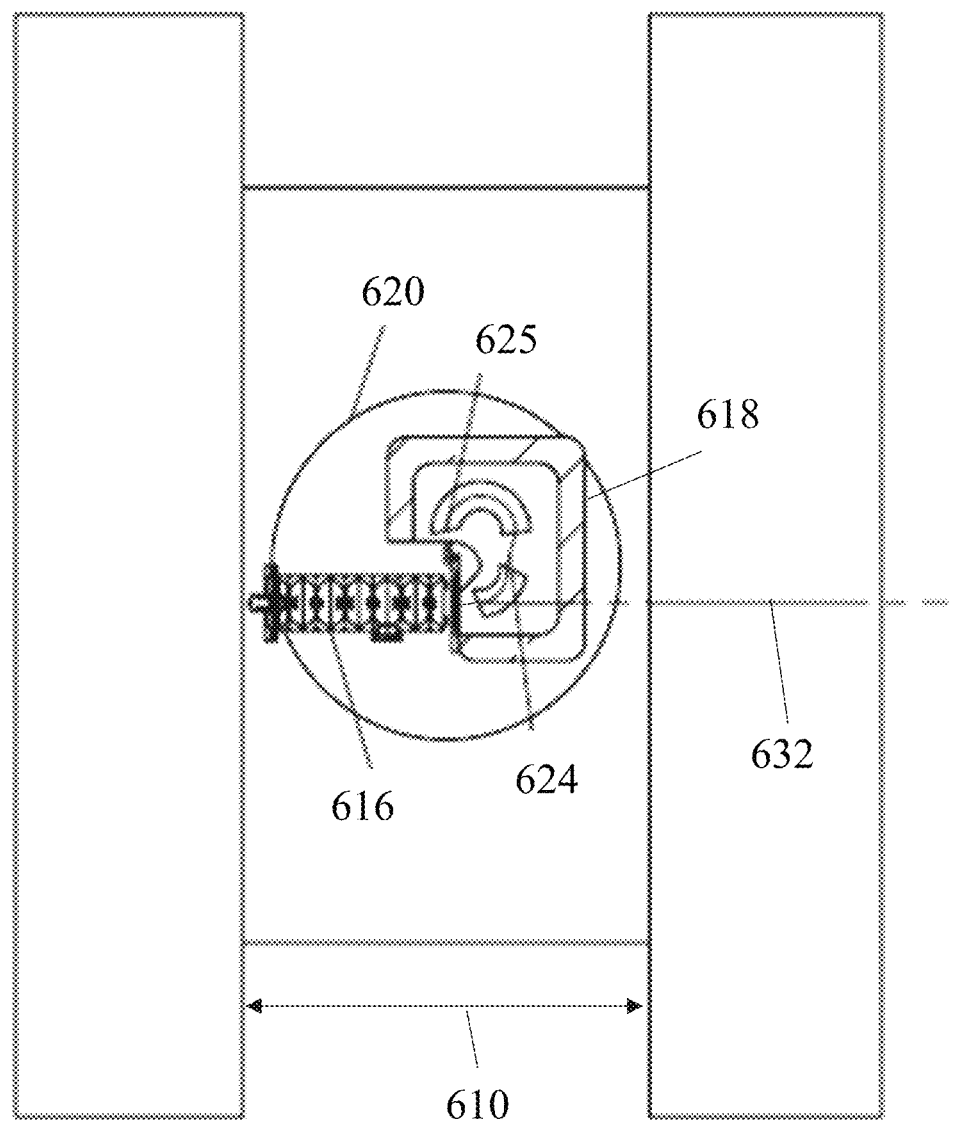
FIG. 8 illustrates a cross-sectional view of a therapeutic apparatus according to some embodiments of the present disclosure.

FIG. 8 illustrates a cross-sectional view of a therapeutic apparatus according to some embodiments of the present disclosure. In some embodiments, the cross-sectional view may be formed by viewing the therapeutic apparatus 600 along a negative direction of the Y axis with reference to the coordinate 630 in FIG. 6.

The linear accelerator 616 may include an accelerating tube which provides a linear path for accelerating the electrons. The accelerating tube may be a travelling-wave tube, a standing-wave tube, etc. In some embodiments, the standing-wave tube may be of an electric coupling type, a magnetic coupling type, etc., according to a coupling manner between the linear accelerator 616 and the microwave device. In some embodiments, the standing-wave tube may be of a single cycle type, a two cycle type, a three cycle type, etc., according to a count (or number) of cycles of the structure of the accelerating tube.

In order to minimize the width of the recess 610, the arrangement of one or more components of the radiation therapy apparatus (e.g., the linear accelerator 616 and the deflection device 618) may be more compact. In some embodiments, the exit window of the linear accelerator 616 may be connected to inlet of the deflection device 618. The electron beam emitted from the linear accelerator 616 may enter the deflection device 618 directly. In some embodiments, the linear accelerator 616 may be located at a center of the recess 610 in the width direction of the recess 610. The treatment head 620 having a shape of a cylinder may also be located at a center of the recess 610 in the width direction of the recess 610. The linear accelerator 616 may be disposed on a flat surface of the cylinder having a larger distance to the axis 606. The flat surface may have a shape of a circle. The linear accelerator 616 may be spaced apart from the center of the flat surface. For example, a distance between the center of the flat surface and a center line of the linear accelerator 616 may be 2 centimeters, 5 centimeters, 10 centimeters, etc. The linear accelerator 616 may connect to the deflection device 618 which deflects the electron beam emitted from the linear accelerator 616 by a deflection angle (e.g., 270 degrees) on the plane parallel to the flat surface. In some embodiments, the width of the recess 610 may be equal to the diameter of the treatment head 620. The width of the recess 610 may be minimized according to the embodiments exemplified above, such that the homogeneity of the magnetic field generated by the plurality of main magnetic coils and the plurality of shielding coils may be improved, and the effect of recess 610 on the imaging of the subject using the MRI apparatus may be removed or reduced. The recess 610 on the cryostat 608 may have an influence on the magnetic field generated by the plurality of main magnetic coils and the plurality of shielding coils. In some embodiments, one or more shim coils may be provided in the magnetic body 602 so as to compensate for the inhomogeneity of the magnetic field generated by the plurality of main magnetic coils and the plurality of shielding coils in the magnetic body 602.

In some embodiments, the deflection device 618 may correct dispersion of the electrons in the electron beam when the electron beam is deflected by a specific deflection angle on the plane parallel to the flat surface of the treatment head 620. The deflection device 618 may include one or more deflection magnets. In some embodiments, one or more parameters of the deflection magnets of the deflection device 618 may be designed so as to correct the dispersion of the electrons in the electron beam. The one or more parameters may relate to the size, structure, material and/or magnetic property of at least one deflection magnet of the deflection device 618. In some embodiments, the one or more deflection magnets may form at least one arc-shaped deflection channel. An inlet of a forefront arc-shaped deflection channel of the at least one deflection channel may be aligned with a centerline 632 of the accelerating tube of the linear accelerator 616. Also, an inlet of a forefront arc-shaped deflection channel of the at least one deflection channel may be aligned with the exit window (i.e., outlet) of the linear accelerator 616. When the electron beam emitted from the linear accelerator 616 passes through the at least one arc-shaped deflection channel, electrons of specific energy values in the electron beam may be deflected by the deflection angle in the at least one arc-shaped deflection channel along a first portion of a moving trajectory 624, and electrons of other energy values in the electron beam may be deflected by different deflection angles such that the electrons of other energy values may not reach an outlet 625 of a rearmost arc-shaped deflection channel (i.e., the outlet of the deflection device 618) of the at least one arc-shaped deflection channel. The first portion of the moving trajectory 624 of the electrons of the specific energy values in the electron beam may be on the plane parallel to the flat surface of the treatment head 620. A radius of each of the at least one arc-shaped channel, a magnetic induction intensity in each of the at least one arc-shaped channel, a gap between magnetic poles of each of the at least one arc-shaped channel, an equivalent length of each the at least one arc-shaped channel, a size of the coil of the at least deflection magnet, etc., may be properly designed such that the electrons of the specific energy values in the electron beam may be deflected by the deflection angle in the at least one arc-shaped deflection channel along the first portion of the moving trajectory 624, and be emitted out from the outlet of the rearmost arc-shaped deflection channel 625 of the at least one arc-shaped deflection channel. Merely for illustration purposes, the outlet of the rearmost arc-shaped deflection channel 625 may coincide with the center of the flat surface of the treatment head when the deflection angle is 270 degrees.

In some embodiments, the deflection device 618 may further include a magnetic shielding component for shielding a magnetic field generated by the plurality of main magnetic coils and the plurality of shielding coils in the deflection channel. In some embodiments, the magnetic shielding component may include one or more magnetic shielding structures that are made of high magnetic susceptibility and/or permeability materials. The magnetic shielding component may include at least one magnetic shielding plate or layer surround or substantially surround the deflection device 618, providing a continuous pathway for the magnetic field to pass through.

Figure 9:
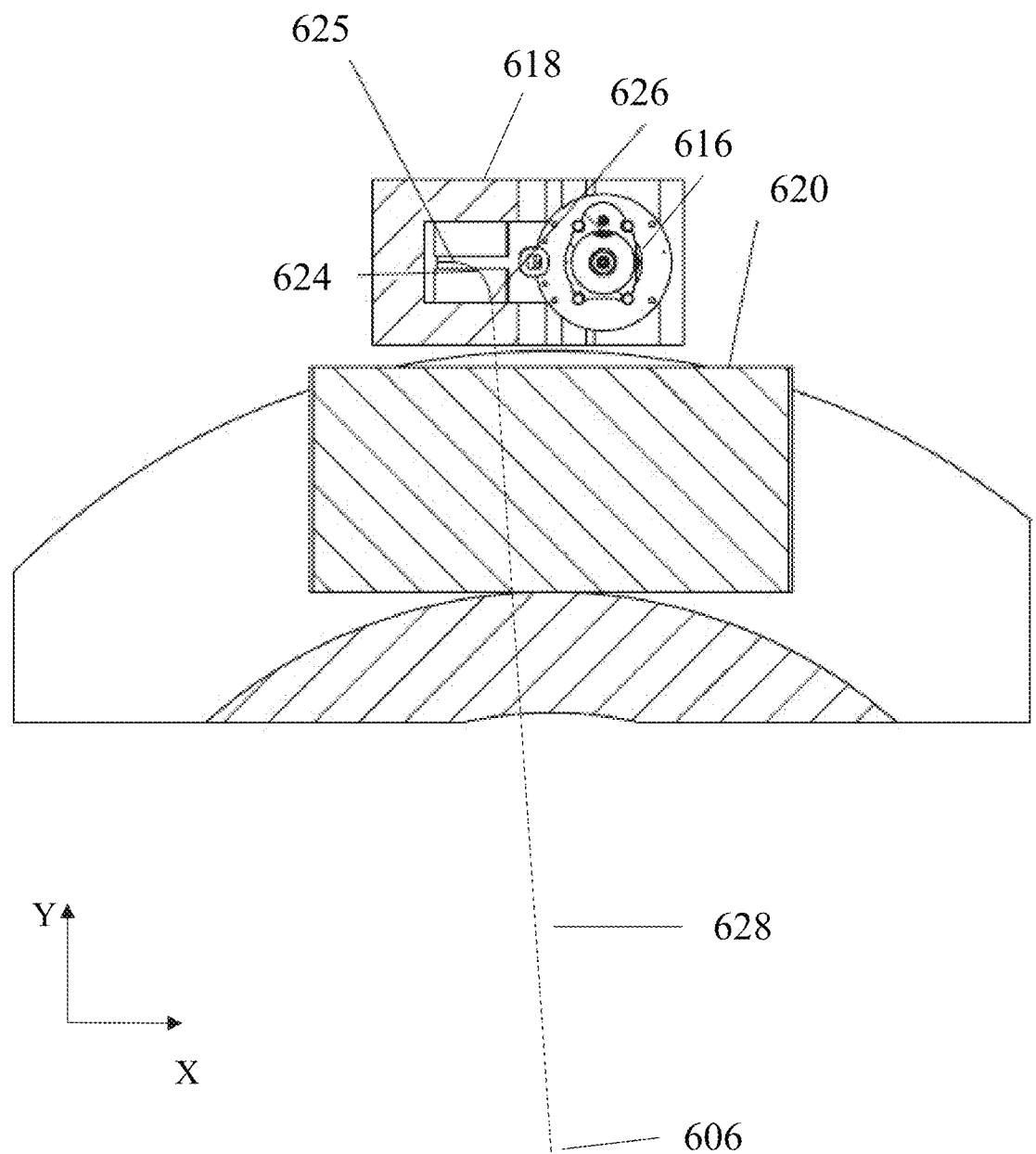
FIG. 9 illustrate a cross-sectional view of an upper portion of a therapeutic apparatus according to some embodiments of the present disclosure.

FIG. 9 illustrate a cross-sectional view of an upper portion of a therapeutic apparatus according to some embodiments of the present disclosure. In some embodiments, the cross-sectional view may be formed by viewing the therapeutic apparatus 600 along a positive direction of the Z axis with reference to the coordinate 630 in FIG. 6.

After the electron beam accelerated in the linear accelerator 616 is emitted out of the deflection device 618 from the outlet 625, the electron beam may be within the magnetic field generated by the plurality of main magnetic coils and the plurality of shielding coils. Since the intersection angle between the direction of the electron beam and the direction of the magnetic field at the outlet 625 is not equal to 0 degrees or 180 degrees, a Lorentz force may be enforced on the electron beam, such that the electron beam may be deflected out of the plane parallel to the flat surface of the treatment head 620 along a second portion of the moving trajectory 624 and collides onto the target 626 substantially vertically.

In some embodiments, the center line of the accelerating tube of the linear accelerator 616 (along the Z direction) may be spaced apart from a line along a radial direction of the MRI apparatus that passes through the target 626. The radial direction may be perpendicular to the axis 606. Merely for illustration, the line along the radial direction of the MRI apparatus that passes through the axis 606 may be illustrated as a line 628 in FIG. 9, which may be along a direction of the radiation beam. In some embodiments, the accelerating tube of the linear accelerator 616 and the target 626 may correspond to different circumferential positions of the MRI apparatus. The circumferential positions may be positions at the cylindrical body of the MRI apparatus.

An electron beam emitted from the linear accelerator 616 may be deflected to the target under the action of magnetic fields generated by the deflection device 618, the plurality of main magnetic coils, and the plurality of shielding coils. In some embodiments, the deflection device 618 may be or include at least one electromagnet. The deflection device 618 may deflect the electron beam of different energy levels to the target 626 along the same trajectory 624. In this case, a length of the accelerating tube of the linear accelerator 616 may be any suitable value. Accordingly, the electron beam emitted from the linear accelerator 616 may have different energy levels (e.g., ranging from 6 Mev to 10 Mev). It should be noted that the direction 628 may include multiple directions since the axis 606 includes a plurality of points.

Figure 10:
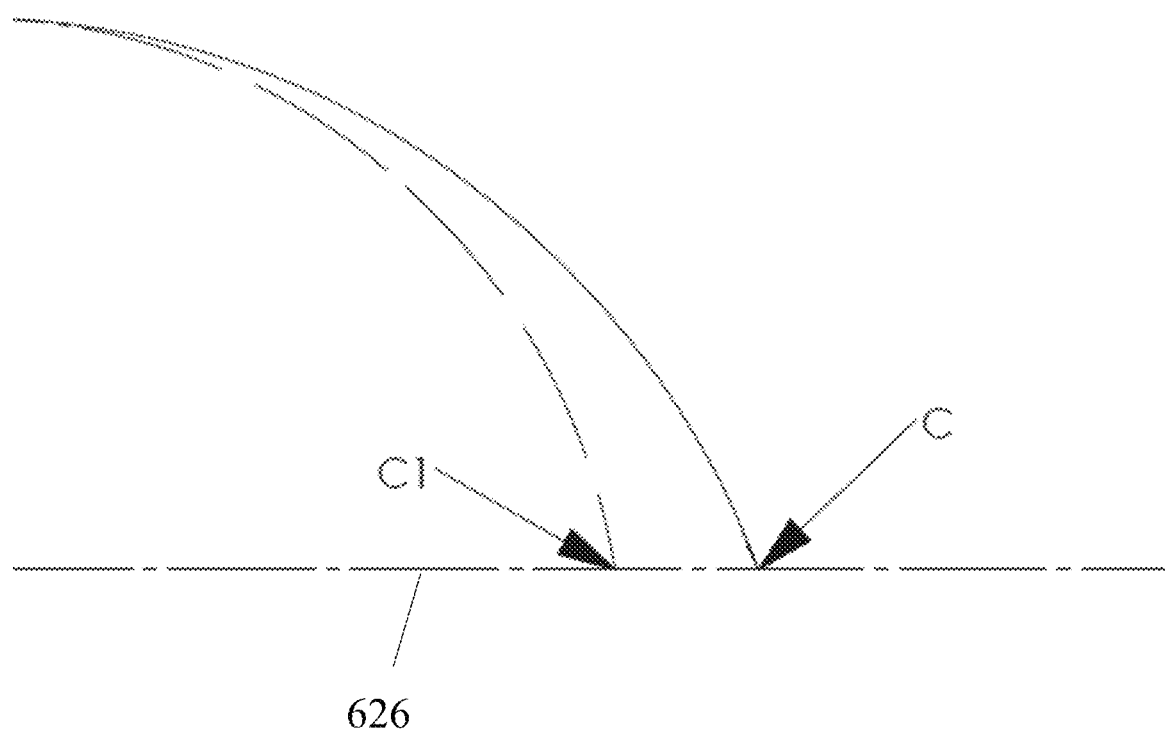
FIG. 10 illustrates a shift of a trajectory of an electron beam in a magnetic field according to some embodiments of the present disclosure.

In some embodiments, in the second portion of the moving trajectory 624 from the outlet 625 to the target 626, the magnetic field generated by the plurality of main magnetic coils and the plurality of shielding coils may be inhomogeneous due to factors of various types, such as manufacturing errors of at least one of the plurality of main magnetic coils and the plurality of shielding coils, fluctuation of the current on at least one of the plurality of main magnetic coils and the plurality of shielding coils, the influence of the recess 610, the influence of the deflection device 618, etc. The second portion of the moving trajectory 624 may shift from a target trajectory to an error trajectory. Merely for illustration purposes, FIG. 10 illustrates a shift of a moving trajectory of an electron beam in a magnetic field according to some embodiments of the present disclosure. As illustrated in FIG. 10, the inhomogeneity of the magnetic field may shift the electron beam from a predetermined trajectory (represented by the solid line in the figure) to an error trajectory (represented by the dotted line in the figure). The electrons in the electron beam transmitted along the predetermined trajectory may collide onto the target 626 at a position C. An angle between the moving direction of the electron beam along the predetermined trajectory and a surface of the target 626 (represented by the dot-dash line in the figure) at the position C may be substantially 90 degrees (i.e., the electron beam collides on the surface of the target 626 perpendicularly or vertically). The electrons in the electron beam transmitted along the error trajectory may collide onto the target 626 at a position C1. An angle between the moving direction of the electron beam along the error trajectory and the surface of the target 626 at the position C1 may not be 90 degrees. In this case, the dose rate of the produced radiation therapeutic beam may be reduced.

In some embodiments, one or more correction coils may be arranged along the moving trajectory 624 of the electron beam (e.g., the first portion between the inlet and the outlet 625 of the deflection device 618 and/or the second portion between the outlet 625 of the deflection device 618 and the target 626. The one or more correction coils may be configured to correct the moving trajectory of the electron beam from the error trajectory to the predetermined trajectory so that the electron beam collides onto the target 626 substantially perpendicularly or vertically. Merely for illustration purposes, the one or more correction coils may be configured along the moving trajectory of the electron beam (i.e., the second portion of the moving trajectory 624).

Figure 11:
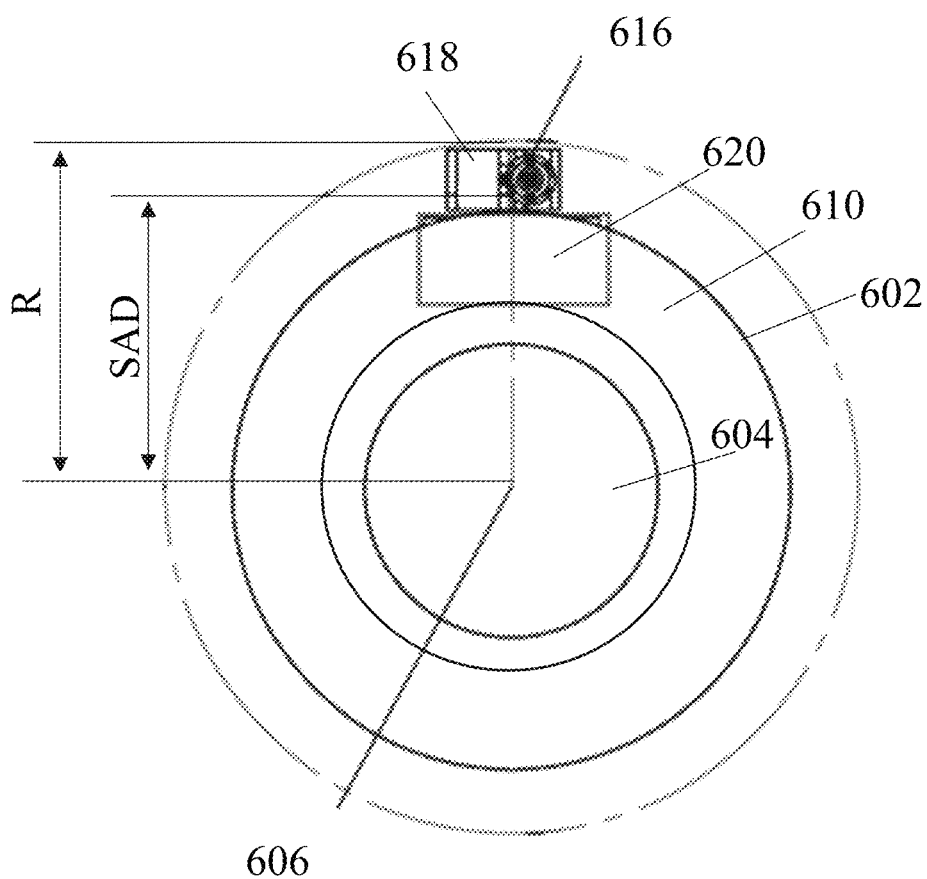
FIG. 11 illustrates a side view of a radiation therapeutic apparatus according to some embodiment of the present disclosure.

FIG. 11 illustrates a side view of a radiation therapeutic apparatus according to some embodiment of the present disclosure. In some embodiments, the side view may be formed by viewing the therapeutic apparatus 600 along a positive direction of the Z axis with reference to the coordinate system 630 as illustrated in FIG. 6.

One or more components of the radiation therapy apparatus of the therapeutic apparatus 600 may be arranged at least in part in the annular recess 610 formed on the outer surface of the magnetic body 602. A source-to-axis distance (SAD) from the target of the radiation therapy apparatus to the axis 606 (i.e., a rotation axis of the gantry) may be about 1 meter, which is smaller than conventional MRI-RT systems, thereby improving a dose rate of the radiation therapeutic beam, and enhancing the therapeutic effect of the target region of the subject. In addition, a radial size R of the therapeutic apparatus 600 from a farthest end of the therapeutic apparatus 600 in the radial direction (e.g., an outer surface of the deflection device 618 having a larger radial distance to the axis 606) to the axis 606 may be about 1.2 meters. It may indicate that an overall size of the therapeutic apparatus 600 may also be smaller than conventional MRI-RT systems, thus benefiting the transportation and assembly of the therapeutic apparatus 600.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by the present disclosure, and are within the spirit and scope of the exemplary embodiments of the present disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A radiation therapy system, comprising:
    a magnetic resonance imaging (MRI) apparatus configured to acquire MRI data with respect to a region of interest (ROI) of a subject, the MRI apparatus including:
        a plurality of shielding magnetic coils, the plurality of shielding magnetic coils being arranged around an axis; and
    a radiation therapy apparatus configured to apply therapeutic radiation to at least one portion of the ROI, the radiation therapy apparatus including:
        a linear accelerator configured to accelerate electrons to produce a radiation beam, the linear accelerator being located between two neighboring shielding coils of the plurality of shielding coils along a direction of the axis, and a length direction of the linear accelerator being parallel with the axis; and
        a deflection magnet configured to deflect the electrons emitted from the linear accelerator by a deflection angle in a first portion of a moving trajectory, the first portion of the moving trajectory being on a plane intersecting with a radial plane of the MRI apparatus, wherein the plane on which the first portion of the moving trajectory is parallel to a platform on which the linear accelerator is located.

2. The radiation therapy system of claim 1, wherein the deflection magnet includes at least one electromagnet, the at least one electromagnet being configured to correct dispersion of the electrons.

3. The radiation therapy system of claim 1, wherein the deflection magnet includes at least one arc-shaped deflection channel on the plane, an inlet of a forefront arc-shaped deflection channel of the at least one deflection channel being aligned with an outlet of the linear accelerator, and the electrons being deflected by the deflection angle in the at least one arc-shaped deflection channel.

4. The radiation therapy system of claim 3, wherein the electrons emitted from a rearmost arc-shaped deflection channel of the at least one arc-shaped deflection channel are deflected to a target in a second portion of the moving trajectory, the second portion of the moving trajectory being within a main magnetic field generated by a plurality of main magnetic coils of the MRI apparatus, the direction of the main magnetic field being parallel with the axis.

5. The radiation therapy system of claim 4, wherein the radiation therapy apparatus further includes one or more correction coils along at least one of the first portion or the second portion of the moving trajectory, the one or more correction coils being configured to correct the moving trajectory so that the electrons collide onto the target substantially vertically.

6. The radiation therapy system of claim 1, wherein the deflection angle is 270 degrees.

7. The radiation therapy system of claim 1, wherein a center line of an accelerating tube of the linear accelerator is spaced apart from a line that is along a radial direction of the MRI apparatus, the line passing through a target.

8. The radiation therapy system of claim 1, wherein an accelerating tube of the linear accelerator and a target correspond to different circumferential positions of the MRI apparatus.

9. The radiation therapy system of claim 1, wherein the MRI apparatus further includes:
  an annular cryostat in which a plurality of main magnetic coils and the plurality of shielding coils are located, the plurality of main magnetic coils, the plurality of shielding coils, and the annular cryostat being coaxially arranged.

10. The radiation therapy system of claim 9, wherein the annular cryostat includes an outer wall, an inner wall, and a recess between the outer wall and the inner wall, the recess having an opening formed at the outer wall, the linear accelerator being at least partially located within the annular recess.

11. The radiation therapy system of claim 9, wherein the recess is a through hole along a radial direction of the MRI apparatus.

12. The radiation therapy system of claim 9, wherein the MRI apparatus further includes:
  one or more gradient coils arranged in a bore formed by the annular cryostat, the one or more gradient coils being around the axis.

13. The radiation therapy system of claim 12, wherein the one or more gradient coils are split gradient coils.

14. The radiation therapy system of claim 1, wherein the plane where the first portion of the moving trajectory is located is substantially perpendicular to a radial plane of the MRI apparatus.

15. A radiation therapy system, comprising:
  a magnetic resonance imaging (MRI) apparatus configured to acquire MRI data with respect to a region of interest (ROI) of a subject, the MRI apparatus including:
    a plurality of main magnetic coils, the plurality of main magnetic coils being arranged around an axis; and
    a plurality of shielding magnetic coils, the plurality of shielding magnetic coils being arranged coaxially with the plurality of main magnetic coils, with a larger radius from the axis than the plurality of main magnetic coils;
  a radiation therapy apparatus configured to apply therapeutic radiation to at least one portion of the ROI, the radiation therapy apparatus including:
    a linear accelerator configured to accelerate electrons to produce a radiation beam, the linear accelerator being located between two neighboring shielding coils of the plurality of shielding coils along a direction of the axis, and a length direction of the linear accelerator being parallel with the axis; and
    a deflection magnet configured to deflect the electrons emitted from the linear accelerator by a deflection angle in a first portion of a moving trajectory, the first portion of the moving trajectory being on a plane intersecting with a radial plane of the MRI apparatus,
    wherein the plane on which the first portion of the moving trajectory is parallel to a platform on which the linear accelerator is located.

16. The radiation therapy system of claim 15, wherein the deflection magnet includes at least one arc-shaped deflection channel on the plane, an inlet of a forefront arc-shaped deflection channel of the at least one deflection channel being aligned with an outlet of the linear accelerator, and the electrons being deflected by the deflection angle in the at least one arc-shaped deflection channel.

17. The radiation therapy system of claim 16, wherein the electrons emitted from a rearmost arc-shaped deflection channel of the at least one arc-shaped deflection channel are deflected to a target in a second portion of the moving trajectory, the second portion of the moving trajectory being within a main magnetic field generated by a plurality of main magnetic coils of the MRI apparatus, the direction of the main magnetic field being parallel with the axis.

18. The radiation therapy system of claim 15, wherein a center line of an accelerating tube of the linear accelerator is spaced apart from a line that is along a radial direction of the MRI apparatus, the line passing through a target.

19. The radiation therapy system of claim 15, wherein an accelerating tube of the linear accelerator and a target correspond to different circumferential positions of the MRI apparatus.

* * * * *